_US005370164A_

United States Patent [19]
Galloway

[11] Patent Number: 5,370,164
[45] Date of Patent: Dec. 6, 1994

[54] ASEPTIC FLUID TRANSFER APPARATUS AND METHODS

[75] Inventor: Edwin J. Galloway, Menasha, Wis.

[73] Assignee: Galloway Company, Neenah, Wis.

[21] Appl. No.: 126,692

[22] Filed: Sep. 14, 1993

Related U.S. Application Data

[62] Division of Ser. No. 39,748, Mar. 30, 1993, Pat. No. 5,269,350, which is a division of Ser. No. 787,545, Nov. 4, 1991, Pat. No. 5,199,473, which is a division of Ser. No. 543,747, Jun. 7, 1990, Pat. No. 5,086,813, which is a division of Ser. No. 261,020, Oct. 20, 1988, Pat. No. 4,941,517.

[51] Int. Cl.$^5$ .............................................. B65B 3/04
[52] U.S. Cl. ...................... 141/329; 141/98; 141/312; 141/383; 141/365; 141/367; 141/382; 604/905; 604/403; 206/219; 222/81
[58] Field of Search ............ 141/1, 98, 329, 330, 141/312, 367, 320, 382, 383–387, 363–366, 4, 5, 6, 8, 9; 604/403–407, 415, 416, 905; 206/219; 222/81, 85, 83.5, 83

[56] References Cited

U.S. PATENT DOCUMENTS

| | | | |
|---|---|---|---|
| 3,779,082 | 12/1973 | Galloway | 141/330 X |
| 3,807,467 | 4/1974 | Tascher et al. | 141/375 |
| 3,872,867 | 3/1975 | Killinger | 141/329 X |
| 4,150,673 | 4/1979 | Watt | 141/312 X |
| 4,191,225 | 3/1980 | Ogle | 141/329 |
| 4,347,874 | 9/1982 | Sullivan et al. | 141/1 |
| 4,564,054 | 1/1986 | Gustavsson | 141/329 |
| 4,607,671 | 8/1986 | Aalto et al. | 141/329 |
| 4,697,622 | 10/1987 | Swift et al. | 141/1 |
| 4,941,517 | 7/1990 | Galloway | 141/1 |
| 5,086,813 | 2/1992 | Galloway | 141/1 |
| 5,199,473 | 4/1993 | Galloway | 141/312 |
| 5,269,350 | 12/1993 | Galloway | 141/1 |
| 5,270,219 | 12/1993 | DeCastro | 141/329 X |

FOREIGN PATENT DOCUMENTS 2026992  2/1980  United Kingdom ............... 141/330

Primary Examiner—Ernest G. Cusick
Attorney, Agent, or Firm—Thomas D. Wilhelm

[57] ABSTRACT

Means and apparatus for aseptically transferring material between enclosures. Apparatus for transferring the material includes a fluid receiver assembly (12) comprising an adapter (24), and a fitting (93) mounted in the adapter (24). The fitting has a plurality of needle guide channels (86) leading from the outside of the fluid receiver assembly (12) toward the interior of the enclosure (10), and seal means (26) at the ends of the channels (86). Pierceable, self-closing seal means (26) is between ends of each of the channels (86) and the interior of the enclosure. Projected extensions of the channels pass through corresponding holes (40) in the adapter, so that needles (101) inserted into the channels (86) can penetrate the seal means (26) and enter the interior of the enclosure (10). A plurality of needles (101) in a novel needle bundle (95) may be used in making the transfer. An assembly for transferring material between two stationary enclosures comprises a pair of novel needle bundles (295) and connecting tubing (266). Methods of transferring materials are taught.

24 Claims, 16 Drawing Sheets

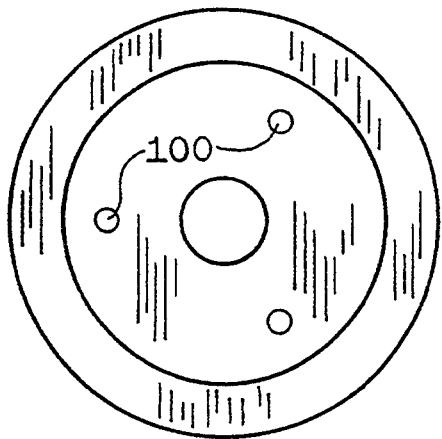
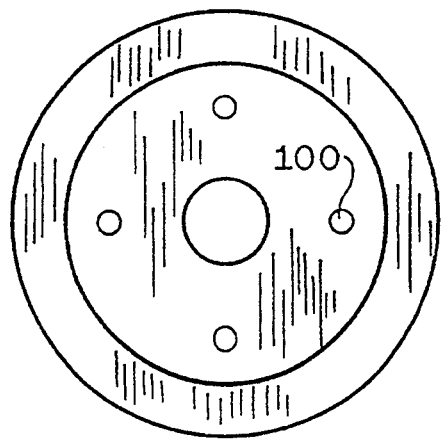
FIG. 14A  FIG. 14B
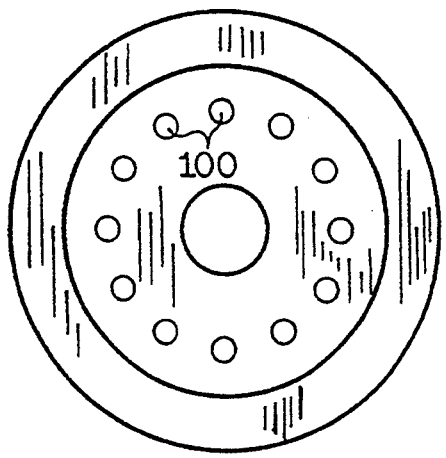
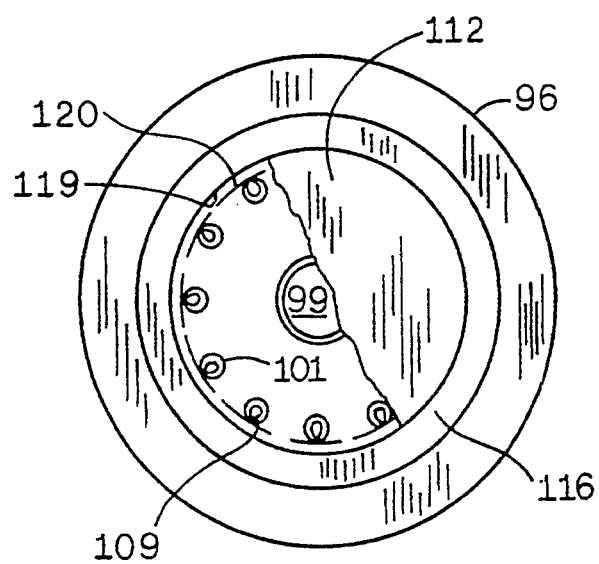
FIG. 14C  FIG. 15

ASEPTIC FLUID TRANSFER APPARATUS AND METHODS

This is a division of application Ser. No. 08/039,748, filed Mar. 30, 1993 U.S. Pat. No. 5,369,350 which is division of 07/787,545 filed Nov. 4, 1991, U.S. Pat. No. 5,199,473; which is a division of 07/543,747 filed Jun. 7, 1990, U.S. Pat. No. 5,086,813; which is a division of 07/261,020 filed Oct. 20, 1988, U.S. Pat. No. 4,941,517.

BACKGROUND OF THE INVENTION

This invention pertains to aseptic systems and their use for transferring fluid into, or out of, an enclosure such as a tank, a pipe, or other type of enclosure vessel, or between enclosure vessels. The invention pertains, for example, to transferring fluids into process systems which are sensitive to contamination from the outside environment.

Particularly this invention pertains to transferring higher viscosity fluids, such as bacteria cultures, starter materials, mother cultures, additives and the like, into processes where the combination in the enclosure is further processed in an aseptic environment. In such processes, contamination of either the fluid transferred, or the other process material into which the fluid is transferred, is unacceptable. Similarly, the invention pertains to transferring such fluids between tanks, and other enclosures, such as components of one or more processing systems.

The word "enclosure" as used herein refers to any closed containment structure without respect to its size. Thus it includes such small enclosures as cans which may be used in shipping starter bacteria from a culture lab. On the other end of the size spectrum, it includes large tanks, which may have capacities of several thousand gallons, or more, such as are used in the dairy processing industry.

Hereinafter, the invention is described with respect to its application to the processing of dairy products. It is contemplated that both the apparatus of the invention and the methods of the invention have application to a wide variety of particularly industrial processes which require the transferring of fluid components without introducing contaminating material into a processing enclosure. While the description concentrates on the use of the invention in the dairy industry, it is appreciated that similar applications can be made in other industries in light of the description of the invention herein.

In the processing of dairy products, and particularly that processing which uses bacterial cultures, the processor typically obtains a container of culture media from a culture supplier. The culture media is introduced into a "mother culture tank" where it is multiplied significantly in volume, and then distributed to the next processing stage in the dairy processing plant for the various processing operations. It is conventional practice to receive the culture media from the supplier in a metal can or similar container. In introducing the culture into the mother culture tank, the can is opened and the contents poured into the tank through an open port. This process of opening the can exposes the contents of the can to the outside environment. Opening the port on the mother culture tank exposes the inside of the mother culture tank, and culture media in the mother culture tank, to the outside environment. The combination of exposing both the mother tank and its culture media, and the contents of the culture can, to the outside environment and its inherent supply of contaminants, carries substantial risk of introducing airborne organisms such as bacteriophage or the like into the process. This is particularly critical since the general process of the operation is designed to encourage growth of "desirable strains of" bacteria.

Some processors have addressed the problem of contamination at the step of introducing the culture media to the mother tank by attempting to keep sterile the room in which the mother tank is housed. As is well known, sterile conditions are fairly successfully achieved for smaller spaces and volumes. But as the size of the space being sterilized increases, the cost of sterilizing practices increases significantly and the accompanying effectiveness of sterilizing practices decreases. Thus sterile room practices are not entirely satisfactory as (i) they are generally too costly, and (ii) adequate sterility may not be achieved.

Other processors have addressed the contamination problem in other ways, as by attempting to further control the amount of bacteria immediately adjacent the open port. In one method of controlling the bacteria around the open port, a ring of fire is generated around the open port by, for example, a natural gas burner device, whereby it is contemplated that bacteria in the vicinity of the open port are destroyed by the heat of the fire. The fire may also have a destructive effect on bacteria which may become attached to the culture as the culture is being poured through the port. However, the same heat which may be destructive to undesired bacteria in the environment as it is passing through the ring of fire may also be destructive to some part of the desired culture bacteria as it is being passed through the fire ring while being introduced into the tank through the open port. At least one supplier suggests that the culture can contents should be still partly frozen when added to the prepared culture medium in the tank.

As alternatives to the use of a fire ring, some processors have been known to use a steam ring in place of the fire ring. In addition some use of chlorination procedures around the opening is also known.

Another problem in the dairy processing industry is that the valves and pumps typically used to transfer, for example, the processed material from the mother culture tank to the processing tanks are difficult to keep clean and sanitized. And so special techniques, such as steam tracing and steam jacketing of pumps and valves, have been developed to assure the maintenance of aseptic conditions. But these are time consuming and expensive procedures, requiring a high level of training and skill on the part of the operator, as well as the operators' alert attention. Along with such complex procedures goes the risk of human error, whereby contaminated product might be produced and shipped—to the processor's detriment and liability. So the process is not only complex and costly, it also carries a risk of failure by virtue of its complexity. Further, such techniques carry environmental costs to air condition plants containing such steam processes. Plus, workmen can easily be burned by the hot equipment.

Thus it would be desirable to have a method of transferring material into and out of an enclosure which is sensitive to contamination from the outside environment, and to make those transfers in an assuredly aseptic manner. And it would be desirable to have apparatus appropriate for facilitating such transfers.

It is an object of this invention to provide apparatus for transferring a composition into or out of an enclosure while assuring the maintenance of the aseptic condition in the enclosure and preventing the introduction of contaminants into the enclosure, or into the process material, in the process of making the transfer.

It is another object to provide a method of making such an aseptic transfer.

It is yet a further object to provide necessary fittings and associated components to affect the fluid transfer through a fluid receiver assembly and a needle bundle assembly.

It is yet another object to provide a needle holder for holding needles in a needle bundle assembly. The needle bundle assembly facilitates the smooth functioning of the process of inserting the needles through the fluid receiver assembly into the interior of the enclosure.

It is still another objective to provide novel apparatus and means for transferring material from one stationary tank to another tank, without exposing the interior of either tank, or the material being transferred, to the outside environment.

SUMMARY OF THE INVENTION

The invention comprehends novel systems and methods, both containing novel elements, for aseptically transferring fluids between enclosures. In one respect, the invention is seen in an adapter for use in an enclosure. The adapter comprises an outer wall portion, a central core member, a plurality of spaced holes through the adapter, and means for mounting a fitting to the adapter. The holes are disposed between the outer wall portion and the core member, and pass through hard material not normally penetrable by conventional hypodermic needles. Preferably, the adapter has a top, a bottom, and an annular channel means between the outer wall portion and the central core member, with the annular channel extending downwardly from the top toward the holes. Desirably, the bottom portion of the channel means is segmented and the channel segments taper toward the holes, such that, the cross-sectional areas of the channel segments decrease as they approach the orifices of the holes. The holes are desirably disposed toward the bottom of the adapter.

In some embodiments, the cross-section of the core member increases from the top toward the bottom. Portions of the core member may converge with portions of the channel segments.

The channel means may have an outer periphery on the inner surface of the outer wall portion wherein the outer periphery has a plurality of secondary channels extending downwardly toward the holes.

The adapter may include bridging walls between the holes, the bridging walls extending from the narrowest openings of the holes toward the top.

In some embodiments, the annular channel means may comprise a plurality of downwardly directed channel rings spaced, one inside another, between the outer wall portion and the central core member. Thus the adapter may comprise an upstanding outer wall portion defining a perimeter of the adapter, a plurality of spaced holes through the adapter, upstanding bridging walls extending upwardly between the holes, upstanding bridging ribs extending upwardly between rows of the holes, and means, such as a threaded retainer, for mounting a fitting to the adapter.

In another respect, the invention is seen as a resiliently deformable seal member comprising first and second generally opposing surfaces. The first surface comprises a first upwardly projecting central portion, a second upstanding wall portion, and a third penetration zone between the central portion and the wall portion. The second surface comprises first bottom portions opposing, and preferably aligned with, the penetration zone, a second wall portion extending outwardly and upwardly from the first bottom portions, and a third central surface portion extending inwardly and upwardly of the first bottom portions. The composition of the seal member between the penetration zone and corresponding ones of the bottom portions comprises pierceable, self-closing material.

Preferably, the second surface includes fourth wall portions extending upwardly between adjacent ones of the bottom portions. It is also preferred, in some embodiments, that the first central portion on the first surface be convex and the third central portion on the second surface be concave.

The penetration zone may comprise individual recesses aligned with individual ones of the bottom portions. The seal member may include blocking walls extending from the bottoms of the recesses toward the top of the seal member.

The seal member may comprise a wall about its perimeter, extending upwardly to a height "h" from the bottom, a plurality of penetration zones inside the perimeter wall, and blocking rings between ones of the penetration zones, the blocking rings extending upwardly from the penetration zones.

In another respect the invention comprehends a channel member comprising first and second generally opposing surfaces. The first surface comprises a first bottom portion, a second upstanding wall portion disposed outwardly of the bottom portion and a third central portion disposed inwardly and outwardly of the bottom portion. The channel member includes a plurality of needle guide channels extending from the second surface toward the first bottom portion. The axes of the needle channels may diverge from each other from the second surface toward the first surface. The channel member may have a central axis extending between the first and second surfaces, and wherein the needle channels have portions which comprise surfaces most closely approaching the central axis along the lengths of the needle channels, which surfaces diverge from the central axis, as viewed from the second surface toward the first surface. The axes of the needle channels in the channel member may diverge from each other.

The channel member can include flow relief recess means on its first surface.

The first bottom portion may include a base surface, and projections extending from the base surface and about the ends of the needle channels.

In some embodiments, the bottom portion of the channel member comprises a plurality of recessed grooves between rows of the needle channels. Flow relief recesses are preferably adjacent the needle channels. Preferably a flow relief means is adjacent each needle channel, for receiving a flowable material, such as rubber or elastomer, when pressure is applied to the flowable material.

Another aspect of the invention is seen in a fluid receiver fitting. The fitting has a top and a bottom, a readily pierceable film over the top, and a plurality of needle channels extending from the top toward the bottom. The channels extend through a hard material which is not readily pierceable by conventional hypodermic needles. The fitting includes pierceable, self-closing seal means on bottom ends of the needle channels. In some embodiments, the fitting may be defined as including a central axis extending between the top and the bottom, and wherein the needle channels diverge from the central axis, from the top toward the bottom. Also, the axes of the needle channels may diverge from each other, from the top to the bottom. Further, those needle channel surfaces most closely approaching the central axis, and extending along the lengths of the needle channels, may diverge from each other, from the top toward the bottom. In some embodiments, projections of the hard material, at the ends of the channels, are received in recesses in the seal means.

The seal means on the fitting may comprise bottom portions on the bottom of the fitting, and wall portions extending upwardly between adjacent ones of the bottom portions. Preferably, there is an interface between the hard material and the seal means, and blocking walls between the recesses, to impede leakage of fluid between the needle channels at the interface.

The fluid receiver fitting may also be defined as comprising a resiliently deformable seal member, a channel member, and a film covering an outer surface of the channel member, the fitting having a central axis through the seal member and the channel member, the seal member having a first outer surface and a first inner surface, the channel member having a second outer surface and a second inner surface. The first inner surface comprises a first central portion, a second upstanding wall portion, and a third penetration zone between the central portion and the upstanding wall portion. The second inner surface on the channel member comprises a first surface portion in contact with the penetration zone. The first outer surface comprises first bottom portions opposing, and aligned with, the penetration zone, a second upstanding wall portion extending outwardly from the first bottom portion, and a third central surface portion extending inwardly and upwardly of the first bottom portions. The composition of the seal member between the penetration zone and the bottom portions comprises a pierceable, self-closing material. The channel member has a plurality of needle guide channels extending from the second outer surface toward the first surface portion, the needle guide channels being oriented and positioned such that needles inserted into the channels from the second outer surface pass, along paths, through the needle channels, the penetration zone and the bottom portions of the seal member. Optional projections on the first surface portion of the channel member are received in recesses in the seal member penetration zone. The recesses are aligned with the bottom portions whereby the needle guide channels are oriented and positioned in alignment with the bottom portions on the first outer surface.

In some embodiments, each path has a longitudinal axis which diverges from the central axis, from the second outer surface toward the second inner surface.

When the projections on the first surface portion of the channel member are received in recesses in the seal member penetration zone, the recesses being aligned with the bottom portions, the needle guide channels are thus oriented and positioned in alignment with the bottom portions on the first outer surface.

In some embodiments, the bottom portions of the first outer surface are aligned with those surfaces of corresponding ones of the channels, extending along the length thereof, which surfaces most closely approach the central axis of the fitting.

In the receiver fitting, it is preferred that the sum of the narrowest cross-sections of the channels, less the cross-sections of the walls of needles sized to fit the channels, equals at least the cross-sectional area of a tube having an inside diameter of about 0.5 inch, preferably at least about 0.75 inch.

Still another aspect of the invention is a fluid receiver assembly comprising wall means having a plurality of spaced holes through a first hard material which is not readily pierceable by conventional hypodermic needles, channel means having needle channels extending through a second hard material which is not readily pierceable by conventional hypodermic needles, seal means disposed between the channel means and the wall means, and retaining means retaining the channel means to the wall means. The seal means includes pierceable portions, readily pierceable by conventional hypodermic needles. The pierceable portions extend between the needle channels and corresponding ones of the holes. Preferably, the seal means has a bottom surface comprising bottom elements of the pierceable portions extending into the holes, and wall portions between adjacent ones of the bottom portions, the wall portions extending toward the channel means.

The fluid receiver assembly may be perceived as comprising an adapter as described above, a channel member as described above, a seal member as described above, disposed between the channel member and the adapter, and retaining means retaining the channel member to the adapter. Thus, the assembly comprises a plurality of definable needle paths, each needle path extending in a generally singular direction through one of the needle channels, through a corresponding pierceable portion of the seal member, and through a corresponding one of the holes in the adapter. In some embodiments, needles simultaneously resident in the paths are spaced from each other by the central core member and bridging members, both in the adapter. The relative singular directions of the paths may be such that a plurality of needles simultaneously resident in the paths diverge from each other, when considered in a direction extending from the channel member toward the adapter.

The bottom surface of the seal member preferably comprises bottom elements of the pierceable portions extending into the holes in the adapter. Wall portions of the seal member extend toward the channel member between adjacent ones of the bottom portions.

The smallest distance "X" across the holes in the adapter is preferably no more than about three times the smallest distance across the corresponding needle channels in the channel member. It also is preferably no more than about three times the smallest distance across the needles anticipated to be used with the fluid receiver assembly.

Preferably the channel member and seal member are in interfacial contact over substantially all of their facing surface area, and the seal member and adapter are in interfacial contact over substantially all of their facing surface area, with the seal member being held in compressive contact between the adapter and the channel member by a retaining means bridging the channel member and the adapter. The flow relief recesses will generally not be in contact with the seal member when needles are not present in the seal member.

Preferably, the seal member is compressed between the adapter and the channel member, the pierceable portions of the seal member having outer surfaces extending through the holes and beyond the bottom surface of the adapter.

Preferably, the retaining means has an inner annular opening and a flange thereabout, the opening receiving a corresponding annular outer surface of the channel means dimensioned to fit snugly in the annular opening of the retaining means. The flange on the retaining means abuts a flange about the channel means for the retaining of the channel means to the wall means. In the fluid receiver assembly, the needle channels are typically aligned with the holes.

The invention is further perceived as an enclosure for enclosing a fluid. The enclosure comprises wall means having a plurality of spaced holes through a first hard material as in the adapter described herein, channel means as described herein, seal means as described herein and disposed between the channel means and the wall means, and retaining means retaining the channel means to the wall means. The enclosure may be perceived as comprising an aseptic fluid receiver assembly as described above, with the first wall means serving as an interface with the enclosure. Preferably the needle channels are aligned with the holes and the pierceable portions. The adapter is typically permanently attached to the enclosure.

The fluid receiver fitting preferably comprises a seal means and a channel member cooperatively engaged with each other.

The pierceable, self-closing seal means on the inner ends of the channels are preferably aligned with surfaces of corresponding ones of the channels, which surfaces extend along the lengths of the channels, and which surfaces most closely approach the central axis of the fitting.

In some embodiments, the seal means includes an outer surface disposed away from the channels, the outer surface including bottom portions, and wall portions extending in a direction outwardly of the enclosure between adjacent ones of the bottom portions. The fitting preferably comprises the seal member, having a first inner surface, cooperatively engaged with the channel member, having a second inner surface, a first central portion of the first inner surface being convex, the second inner surface comprising a central concave portion.

In some embodiments, the outer surface of the seal member, which is disposed inwardly toward the enclosure, has a central surface portion extending outwardly of the enclosure from the innermost portions of the seal member, and engaging the central core member of the adapter, the seal member being compressively held between the channel member and the adapter. In the most preferred embodiments, the fitting is compressively retained to the adapter by a retaining means bridging the outer surface of the fitting and an outer ring on the adapter, and wherein the retaining means provides means for the compressive retaining of the fitting to the adapter.

Yet another aspect of the invention is seen in a novel needle holder comprising first and second ends, and a plurality of needle holding channels extending between the first and second ends. The first end has a spacer extending from it, for spacing the first end from a generally planar surface over a distance functional to provide a curvilinear adapting region for needles extending through the needle holder in a first direction, and extending beyond the spacer in a modified second direction which comprises a small angle, for example less than 15°, preferably less than about 10°. A typical angle can be scaled from the drawings, for example FIG. 16.

In some embodiments of the needle holder, it is preferred that the spacer hold the first end spaced from the surface by a distance of about 0.25 to about 0.65 times the distance between the first and second ends of the needle holder. Preferably the needle holder includes a first joinder means for joining together the needle holder and a needle cover extending from the first end, such that the cover cannot be removed by an adult of average strength without the use of a tool. The joining means is preferably adjacent the first end for joining with joinder means of an abuse resistance needle cover extending from the first end.

Preferred embodiments of the needle holder include means on the needle holder for cooperatively orienting the needle holder with respect to a receiver capable of receiving and orienting the needle holder.

Still another aspect of the invention is seen in a needle bundle. The needle bundle comprises, in general, a needle holder, and a plurality of needles in the needle holder. The needle holder has a plurality of needle holding channels extending between first and second ends, and a central axis extending between the first and second ends. First needle ends extend from the first end of the needle holder. The first needle ends have first angled surfaces providing first end points. The first angled surfaces are disposed in directions transverse to the lengths of the needles, and toward the central axis of the needle holder. The needle bundle preferably includes a difficultly and resiliently compressible, abuse resistant cover joined with the needle holder and extending outwardly beyond the first end of the needle holder and beyond the first ends of the needles.

The needle bundle can further comprise a bacteria-impermeable cover covering those portions of the needles extending from the first end of the needle holder, the bacteria-impermeable cover being readily pierceable by the needles.

Especially when the needle bundle comprises a large number of needles, the first ends of the needles may be staggered, that is, the needle ends extend different distances from the first end of the needle holder. Preferably no more than 50%, most preferably no more than ⅓, of the needles extend the same distance from the end of the needle holder.

In certain embodiments of the needle bundle, second needle ends, extending from the second end of the needle holder, have second angled surfaces providing second end points. The second angled surfaces are disposed in directions transverse to the lengths of the needles, and away from the central axis of the needle holder.

In preferred embodiments, the cover means comprises first joinder means cooperating with second joinder means on the needle holder, thereby joining the cover means and the needle holder. The abuse resistant cover is preferred to be difficultly and resiliently compressible with respect to the lengths of the needles, and may comprise a spring. Extensions of the needles do not intersect the abuse resistant cover means. Rather, the abuse resistant cover is preferred to have an outer end spaced from the first end of the needle holder, the outer end having an opening therein having an inner perimeter so configured that an imaginary perimeter around the outermost ones of the needles adjacent the first ends of said needles can be extended through the opening without encountering the outer end of the abuse resistant cover.

In some embodiments, the second bacteria-impermeable cover means, is attached to the first cover means, preferably at spaced locations of the second cover means, such as by adhesive. In any of the configurations, the bacteria-impermeable cover means is preferably configured to totally enclose those portions of needles extending from one end of a needle holder, and is readily pierceable by needles.

In yet another aspect, the invention comprises a fluid receiver system. The system comprises a fluid receiver assembly in a wall of an enclosure, the fluid receiver assembly comprising a plurality of spaced, but proximate needle paths in a selected configuration having a predetermined orientation, a needle bundle comprising needles arranged to be compatible with the selected configuration and oriented according to the predetermined orientation, and means mounting the needle bundle adjacent the receiver assembly, and capable of driving ends of the needles through the receiver assembly, The needles are oriented according to the predetermined orientation, and positioned such that the ends of the needles are aligned with the needle paths.

In the receiver system, the needle bundle preferably includes an abuse resistant cover over the needles, a first end of the abuse resistant cover having an outer perimeter which fits snugly into an inner perimeter disposed outwardly of the receiver assembly, whereby the alignment of the needles with the needle paths is assured. Also in the receiver system, the mounting means preferably has means for predetermining rotational orientation of other elements of the system relative to itself. Thus, the adapter may be oriented according to orientation predetermined by the mounting means, and the fitting keyed to the predetermined orientation of the adapter. The fitting can then be mounted to the adapter only with the desired orientation. The fitting comprises a channel member having a plurality of channels therethrough, and seal means on one end of the channel member, and disposed between the channel member and the adapter. The seal means is rotationally keyed to the adapter. The channel member is rotationally keyed to the seal means. Thus the needle paths are rotationally keyed to the adapter.

The needle bundle has a needle pattern compatible with the needle paths. The needle bundle is rotationally keyed, on the mounting means, to the rotational orientation of the needle paths predetermined by the mounting means, whereby the combination of the mounting of the receiver assembly and the mounting of the needle bundle, with rotational orientations compatible with each other, assures the proper and cooperative rotational alignment of all members of the receiver assembly, and of the needle bundle. Thus all elements of the fluid receiver system can be mounted only in the correct rotational orientation which enables the needles to be aligned with the needle paths and to be driven along the needle paths.

Still another aspect of the invention is seen in a fluid transfer connector comprising a needle holder having a plurality of needle holding channels extending between first and second ends, a plurality of needles in the needle holder having first needle ends extending from the first end of the needle holder, and having passages through the needles, and a tubing joined to, and extending from, the second end of the needle holder, the tubing being adapted to carry fluid. The fluid transfer connector preferably includes a difficultly and resiliently compressible, abuse resistant cover joined with the needle holder and extending outwardly beyond the first end of the needle holder and beyond the first ends of the needles. It also preferably comprises a bacteria-impermeable cover covering those portions of the needles extending from the first ends of the needle holder, the cover being readily pierceable by the needles. The needles can, of course, be staggered as discussed above. The tubing is preferably adapted to carry at least as much fluid as the sum of the carrying capacities of the passages in the needles.

The invention is also seen in a fluid transfer assembly comprising a flexible tubing having two ends, and a needle bundle on each end of the tubing, each needle bundle comprising a needle holder having a plurality of needle holding channels extending between first and second ends, and a plurality of needles in the needle holder having first needle ends extending from the first end of the needle holder and passages through the needles. At least one, and preferably both, of the needle bundles has a difficultly and resiliently compressible, abuse resistant cover joined with the respective needle holder and extending outwardly beyond the first end of the needle holder and beyond the first ends of the needles. The associated tubing is adapted to carry fluid transmitted through the passages in the needles. The needle bundles have the options and capabilities described above. A fluid transfer system comprises a fluid transfer assembly connecting a plurality of enclosures together.

The invention is also seen in a method of transferring a material from a first enclosure into a second enclosure. The method comprises the steps of connecting the first enclosure to a first end of a needle bundle, by driving first ends of the needles into the first enclosure, thereby establishing fluid communication through the needles with the interior of the first enclosure, driving second ends of the needles through a fluid receiver fitting, and into the second enclosure, thereby connecting the second end of the needle bundle to the second enclosure, and establishing communicative passages between the first and second enclosures, through the needles, and urging the material from the first enclosure toward the second enclosure with sufficient force to effect the transfer of the material through the communicative passages in the needles. The needles may be spread during the passage through the fitting into the second enclosure. Typically the needle channels diverge from each other such that the needles diverge from each other as the needles pass through the fitting and into the second enclosure.

In some embodiments of this method, the number of needle channels in the fitting is a multiple of the number of needles in the bundle. The method comprises driving a first needle bundle through the fitting, and into the second enclosure, and transferring the material from the first enclosure to the second enclosure, withdrawing the first needle bundle from the fitting, and connecting a container, through a clean needle bundle, to the second enclosure, through previously unused ones of the needle channels in the fitting. The needle channels clearly make possible the passage of the needles to the seal means. Where the needles are to diverge during insertion through the receiver assembly, the needle holder may be defined as having a central axis. The first and second ends of the needles correspond to the first and second ends of the needle holder. The second ends of the needles have angled surfaces providing end points. When the needles are assembled with the needle holder, the angled needle end surfaces are oriented such that the angled surfaces are disposed in directions transverse to the lengths of the needles, and toward the central axis of the needle holder, such that the end surfaces cooperate with the diverging channels in facilitating the diverging of the needle ends.

Where the needle ends are staggered, the needle bundle may be driven through a fluid receiver fitting, using less force in the driving than the minimum amount required for driving all the second ends through the seal member simultaneously.

The first and second needle ends may be driven simultaneously if desired.

The invention is further illustrated by a method of transferring material from a first enclosure into a second enclosure by driving needles of first and second needle bundles into respective first and second enclosures. The needle bundles are connected to each other by a flexible tubing. The tubing is adapted to carry at least about as much fluid as the sum of the carrying capacities of the passages in each of the needle bundles. The material is urged from the first enclosure toward the second enclosure with sufficient force to effect the transfer of the material through the passages in the needles of the first needle bundle, through the tube, and through the passages in the needles of the second needle bundle into the second enclosure. In the above method, the needle bundles are preferably driven simultaneously. The needles are driven into the enclosures through fluid receiver assemblies. Accordingly, the method can include the step of withdrawing, preferably simultaneously, the needle bundles from the first and second enclosures.

A pressure differential may be established prior to driving the needles into the first and second enclosures, preferably with pressure differential adequate to effect the transfer of material from the first enclosure to the second enclosure.

The transfer method of this invention may comprise the steps of mounting first and second needle bundles in oriented alignment with respective first and second receiver assemblies at respective first and second enclosures, establishing a pressure differential between the first and second enclosures, and, after mounting the needle bundles and establishing the pressure differential, simultaneously driving the first and second needle bundles through the first and second receiver assemblies and into the first and second enclosures. Thus, communicative passage between the first and second enclosures is established, through the first and second needle bundles and the tubing. Where the pressure differential is at sufficient level, before the driving of the needle bundles, to effect immediate commencement of transfer of material upon completion of establishment of the communicative passage between the first and second enclosures, transfer begins immediately after the communicative passage is established.

Finally, the invention is seen as a method of transferring material, the method comprising the steps of providing a fluid transfer assembly in a sterile package at the location of the enclosure, for a first use, driving the ends of needles of the needle bundles through receiver assemblies and into the respective enclosures, and effecting transfer of the material through the fluid transfer assembly, withdrawing the needle bundles from the fluid receivers, transporting the fluid transfer assembly, comprising the flexible tubing, away from the location of the enclosure, to a sterilizing facility, sterilizing the fluid transfer assembly at the sterilizing facility, and repackaging the fluid transfer assembly in a sterile package, for transport to a location of enclosure, for a second use.

BRIEF DESCRIPTION OF THE DRAWINGS

FIGS. 14A, 14B, and 14C show end views of needle holders such as that shown in FIG. 14, and illustrate different needle channel patterns.

FIG. 15 shows an end view, with parts cut away, of the needle bundle of FIG. 14, and is taken at 15—15 of FIG. 14.

DETAILED DESCRIPTION OF THE ILLUSTRATED EMBODIMENTS

Figure 1:
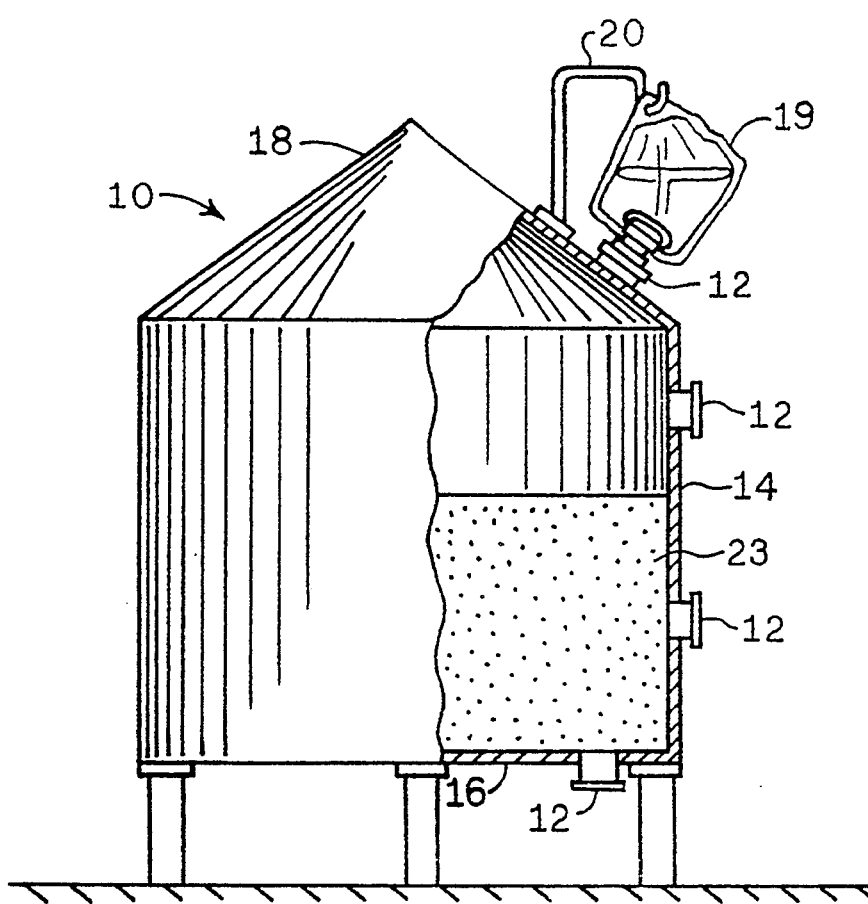
FIG. 1 shows a tank which has fluid receiver assemblies installed in various of the locations contemplated as typical.

FIG. 1 shows a tank 10 typical of those used in the dairy processing industry. Fluid receiver assemblies 12 are seen installed in the sidewall 14, in bottom wall 16 and in top wall 18. A bag 19 of material to be transferred into tank 10 is suspended from a hanger 20, mounted on tank 10, and is communicatively connected to the interior of tank 10, through the receiver assembly 12, by means disclosed more fully hereinafter. The size of the bag is greatly exaggerated relative to tank 10, for visual illustration purposes. The tank is seen to contain material 23 for processing as also is discussed hereinafter.

Figure 11:
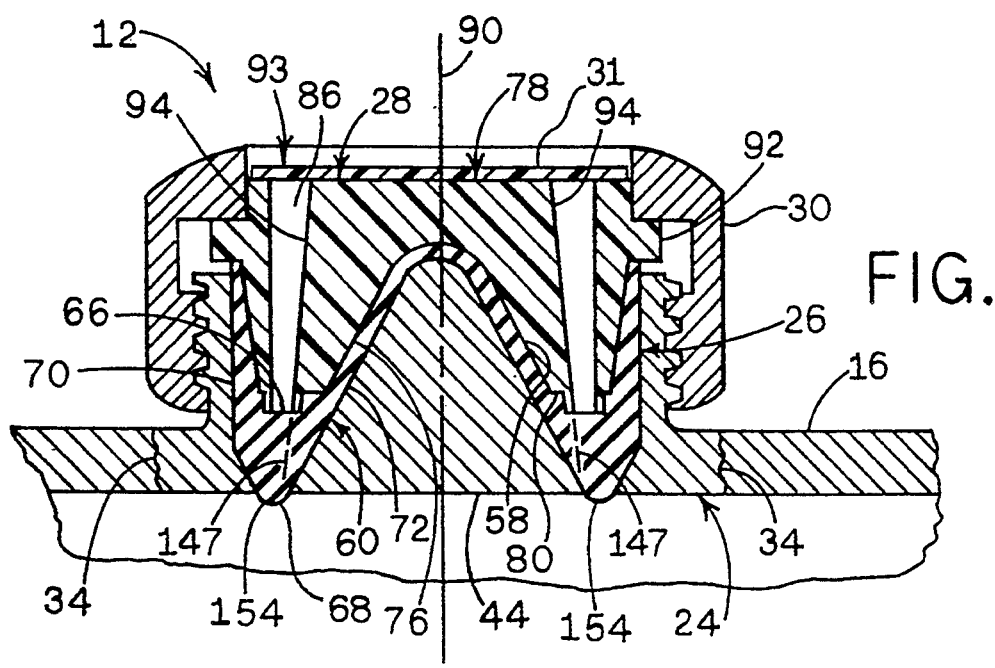
FIG. 11 shows a cross-section of a fluid receiver assembly installed in a wall of an enclosure.

Referring next to FIG. 11, the fluid receiver assembly 12 includes an adapter 24, seal member 26, a channel member 28, a retaining ring 30, and a cover film 31. The assembly is incorporated into a wall of an enclosure such as wall 16 of tank 10 by means of weld 34.

Figure 2:
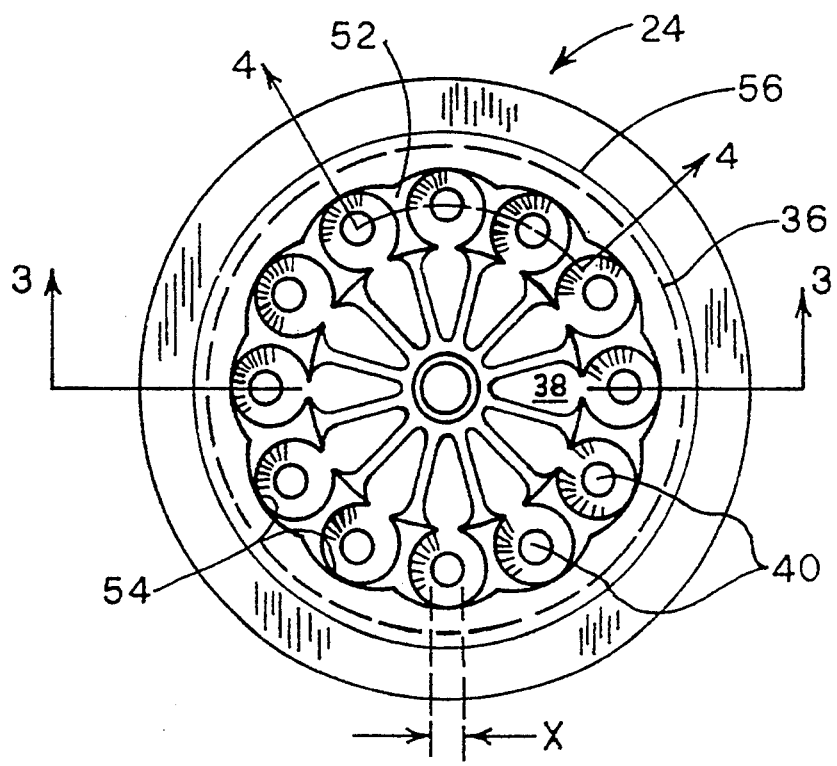
FIG. 2 shows a top view of an adapter useful in the receiver assembly of this invention.
Figure 3:
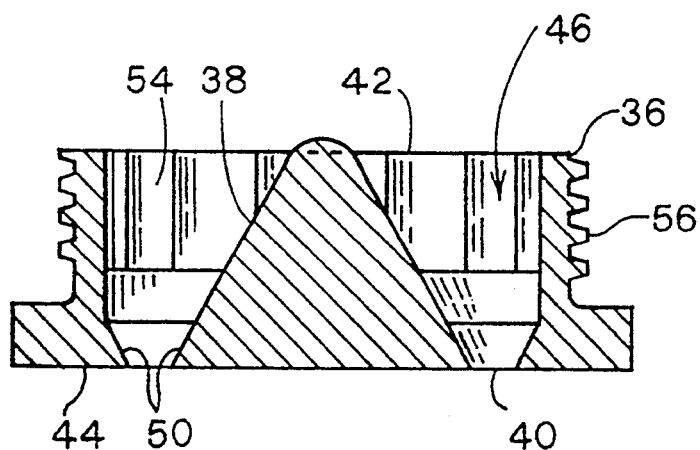
FIG. 3 shows a cross-section of the adapter of FIG. 2 taken at 3—3 of FIG. 2.
Figure 4:
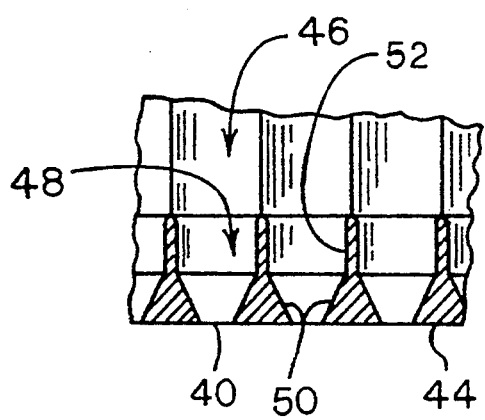
FIG. 4 shows a fragmentary cross-section of the adapter of FIG. 2 taken at 4—4 of FIG. 2.

FIGS. 2, 3, and 4 show the detail of the adapter 24 illustrated in the assembly of FIG. 11. As best seen by the joint consideration of FIGS. 2 and 3, the adapter has an outer wall generally designated 36, a central core member 38, and a plurality of holes 40 between the outer wall 36 and central core member 38.

For purposes of discussing the various features of the adapter, it can be considered to have a top 42 and a bottom 44. The cross-section of central core member 38 is seen to increase progressively from the top 42 toward the bottom 44 of the adapter. Core member 38 is illustrated as generally conical. It could adopt a substantial variety of shapes as will be obvious from the following discussion of the functioning of the adapter in combination with the other components of the invention.

A continuous channel 46 between outer perimeter 36 and central core member 38 extends downwardly from top 42 of the adapter toward holes 40. The bottom of channel 46 is segmented in the sense that it incorporates thereinto holes 40 and the contours leading thereto. The segments 48 of channel 46 taper toward holes 40 as they approach the holes. As best seen in FIGS. 2 and 3, the central core member 38 meets the sidewalls 50 of the channel segments as holes 40 are approached.

A plurality of bridging walls 52 separate the channel segments and, accordingly, holes 40 from each other at, and near, bottom 44 of the adapter, as shown in FIG. 4. Walls 52 also serve as bridges between the outer wall 36 of the adapter, and the central core member. Bridges 52 thus provide the structural support for the adapter interiorly of the outer wall 36.

The outer wall 36 has a plurality of secondary upstanding indexing channels 54 extending upwardly adjacent corresponding holes 40.

Threads 56 on outer wall 36 are used in assembling the fluid receiver assembly as described in more detail hereafter.

Figure 5:
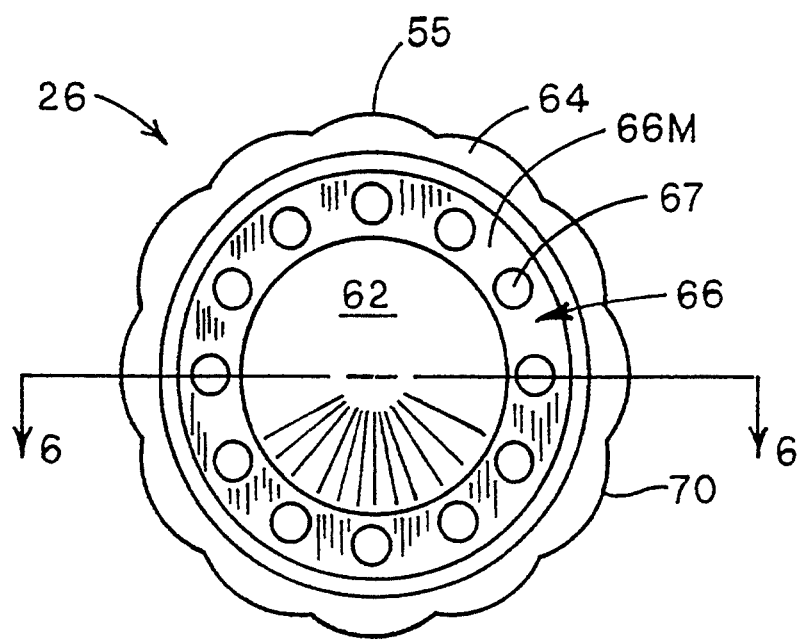
FIG. 5 shows a top view of a seal member of the invention.
Figure 6:
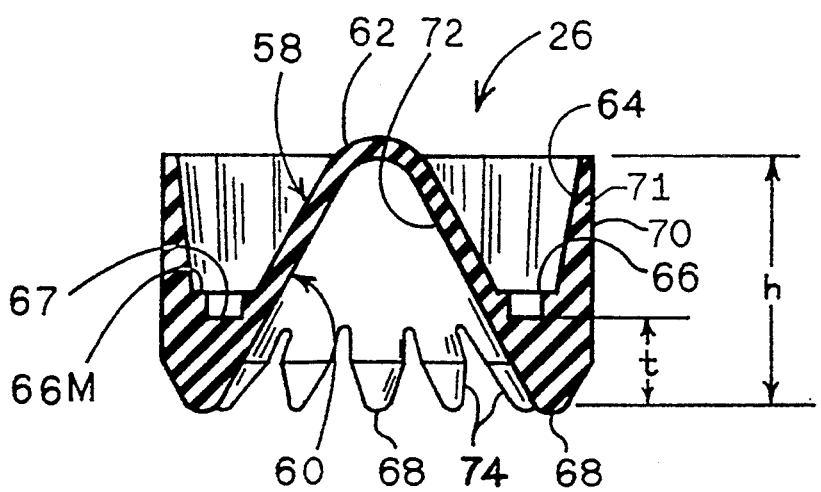
FIG. 6 shows a cross section of the seal member of FIG. 5, taken at 6—6 of FIG. 5.

The seal member 26 is seen generally in FIGS. 5 and 6. Seal member 26 has generally opposing first and second surfaces 58 and 60 respectively. The first surface 58 has a first generally outwardly projecting central portion 62 which is shown convex, and an upstanding outer wall portion 64 generally corresponding to outer wall 36 of adapter 24. Penetration zone 66 is between wall portion 64 and central portion 62. Penetration zone 66 is generally coextensive with the circumference of the first surface at its lower terminus between upstanding wall portion 64 and central portion 62.

Second surface 60 has a plurality of bottom portions 68, an upstanding wall portion 70, and a surface central portion 72. Surface wall portions 74 extend upwardly from, and between, adjacent bottom portions 68, and interface with bridging walls 52 in adapter 24. Walls 74 usually extend upwardly a distance equal to at least 25%, preferably at least 50%, but generally less than 100%, of the thickness of seal member 26 at penetration zone 66, such as between the bottom surface of bottom portion 68 and the surface of penetration zone 66. Bottom portions 68 are aligned with penetration zone 66, as seen further illustrated hereinafter.

Upstanding wall portions 64 and 70 together generally define a wall 71 between them. A plurality of ribs 55 extend upwardly from the bottom of second surface 60 as at bottom members 68.

Wall 71 extends upwardly from bottom portions 68 a distance "h", extending above the lower surfaces of recesses 67. Preferably height. "h" is at least 1.5 times, most preferably at least 2 times, as great as thickness "t", of material between penetration zone 66 and bottom portions 68, whereby penetration zone 66 is shielded, and somewhat protected by wall 71.

Figure 12:
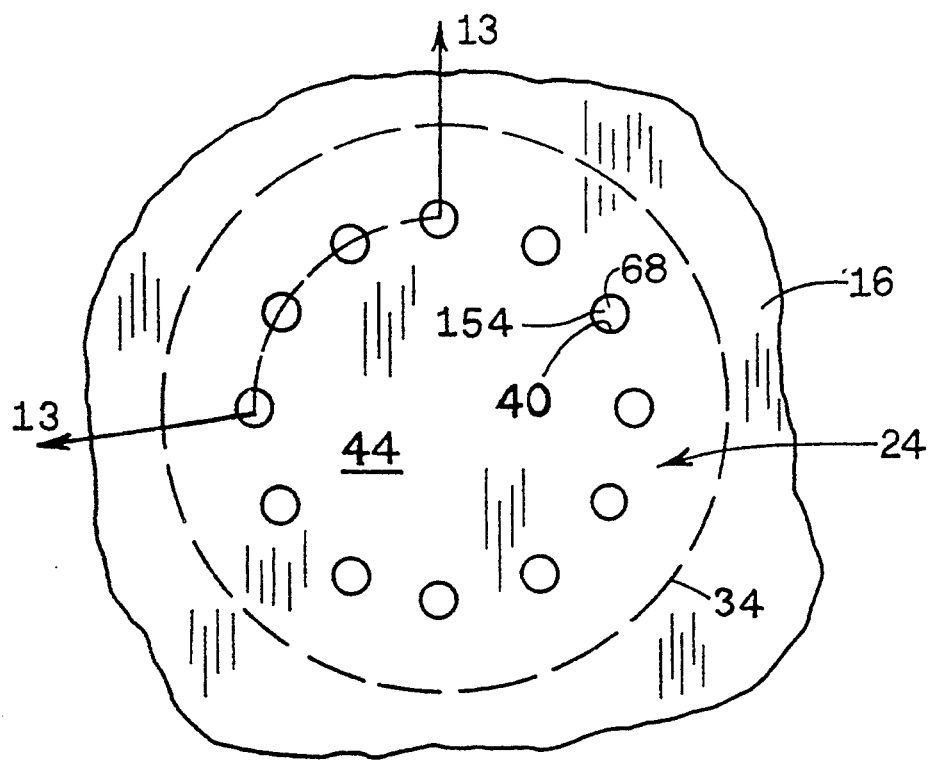
FIG. 12 shows a fluid receiver assembly, as at FIG. 11, as seen from inside the tank.
Figure 16:
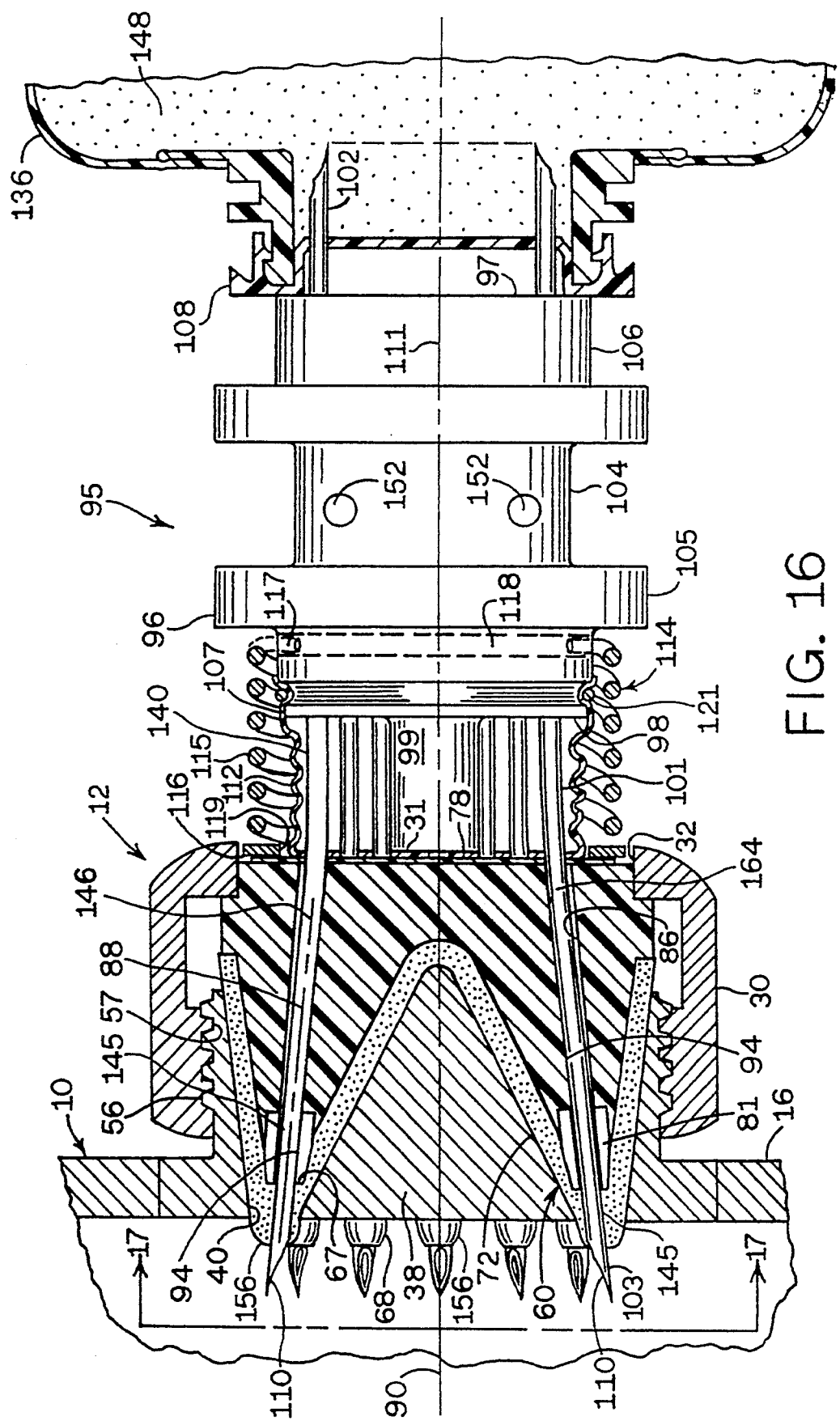
FIG. 16 shows a cross-section of a fluid receiver assembly of the invention installed in a wall of a tank, and a needle bundle connecting a container to the tank.

The penetration zone 66 includes recesses 67 which are aligned with bottom portions 68, One bottom portion 68 fits into each of the holes 40 of adapter 24, as illustrated in FIGS. 11, 12, and 16. In certain embodiments, the penetration zone 66 may be intermittent and non-penetrable about the circumference of the first surface, between areas which correspond to being above the corresponding holes 40 in adapter 24, or between holes 40 and the needle guide channels described hereinafter.

Seal member 26 is made with material that is generally considered to be rubber. And while the compounding of an acceptable rubber composition is believed to be within the skill of the rubber molding art, applicant has found that rubber compounds based on ethylene propylene diene monomer terpolymer (EPDM) are particularly advantageous, with particle size being desirably kept small. EPDM is also known as an elastomer, as will be recognized by those skilled in the polymer arts. And so other elastomers are contemplated, such as those derived from, or modified with, butene, isoprene, ethylene, and the like.

Figure 7:
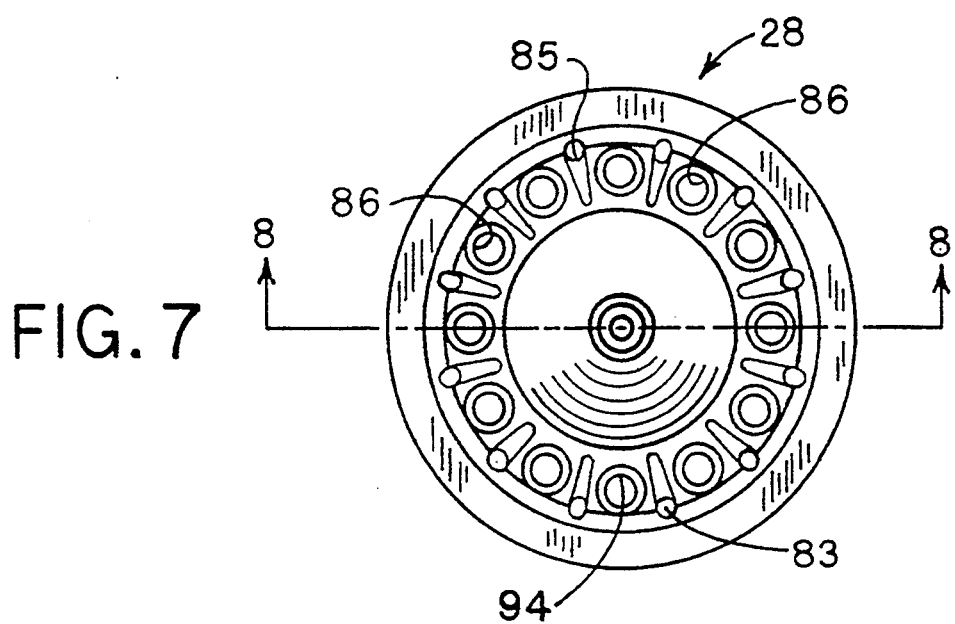
FIG. 7 shows a bottom view of a channel member used in the receiver assembly of the invention.
Figure 8:
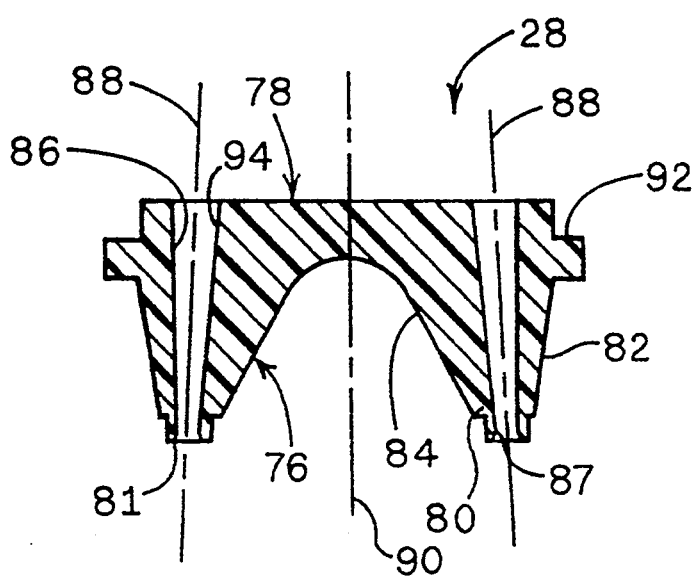
FIG. 8 shows a cross-section of the channel member of FIG. 7 taken at 8—8 of FIG. 7.
Figure 9:
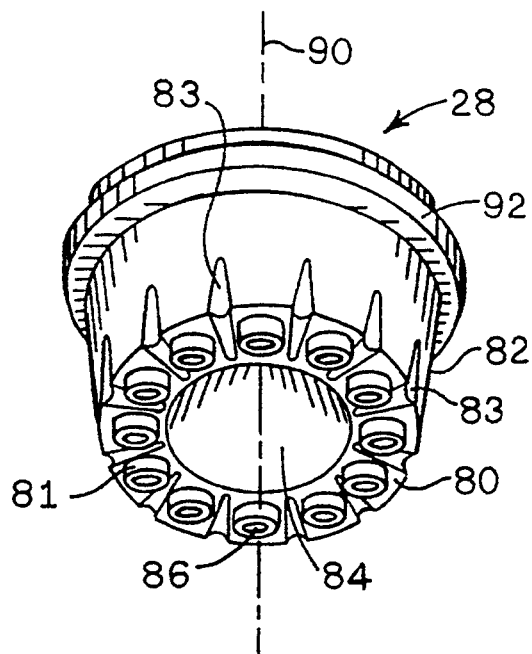
FIG. 9 shows a pictorial view of the bottom of the channel member of FIG. 7.

Referring now to FIGS. 7, 8, and 9, channel member 28 is seen to have generally opposing first bottom and second top surfaces 76 and 78 respectively. First bottom surface 76 has a first bottom portion 80, including optional projections 81, a second upstanding wall portion 82, and a third central portion 84. A plurality of tapered needle guide channels 86 extend between the first and second surfaces and are encompassed, on their lower ends, adjacent bottom surface 76, with projections 81, which include the lower ends of channels 86. Channels 86 are preferably countersunk at their lower, narrower ends as seen at 87 in FIG. 8. As seen in FIG. 8, the axes 88 of the channels diverge from each other, traversing from top 78 to bottom 76, The axes 88 also diverge from central axis 90 of the channel member, when traversing from the top of the channel member as at 78 toward the bottom. Further with respect to FIGS. 7 and 8, it is seen that, in each of needle channels 86, that surface 94 which most closely approaches the central axis 90 also diverges, top to bottom, from central axis 90 along the channel length. Thus is the downward divergence of the channels 86 established with respect to the central axis, with respect to each other, and with respect to the central axis as related to those surfaces 94 of the channels which most closely approach the central axis. Flow relief recesses 83 in bottom portion 80, and in wall portion 82, at the intersection of bottom portion 80 and wall portion 82, are spaced between the respective needle channels 86. The configurations of flow relief recesses 83 are not especially critical so long as they accommodate flow of the elastomeric material of seal member 26 while the channel member provides adequate dimensional structure at its interface with the seal member. Thus recesses 83 can extend further, and in different directions, along wall portion 82. Recesses 83 can also extend entirely across bottom portion 80, as well as into the wall of central portion 84.

Channel member 28 is made of a material that is normally not penetrable by conventional hypodermic needles. A typical material for fabrication of channel member 28 is one of the engineering plastics, such as nylon, polypropylene, or high density polyethylene. The penetrability of channel member 28 is thus provided by the pre-formed needle channels 86, which extend through the channel member from top 78 to bottom 76.

Figure 10:
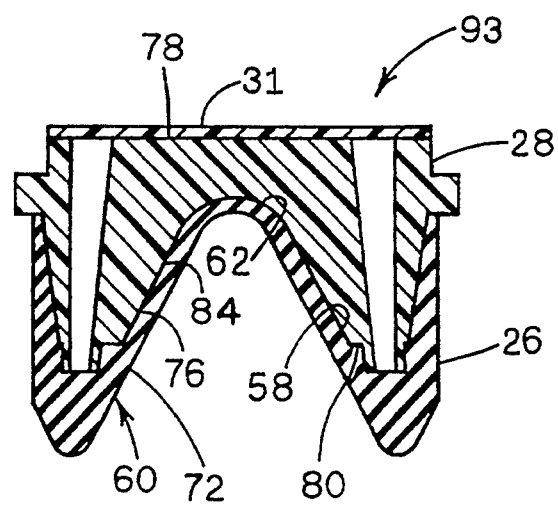
FIG. 10 shows a cross-section of a fitting of the invention.

Fluid receiver fitting 93 is seen in FIG. 10. It comprises the seal member 26, the channel member 28, and the covering film 31, and has a first outer surface corresponding to the second surface 60 as shown in FIG. 6. The first inner surface of the receiver fitting 93 corresponds to the first surface 58 of seal member 26 as described hereinabove with respect to FIG. 6 and seal member 26 alone. The second inner surface of the fitting corresponds to surface 76 of channel member 28. The second outer surface of fitting 93 corresponds in general to surface 78 of channel member 28. In keeping with the relatively small thickness of covering film 31, the second outer surface of the fitting generally includes the entire thickness of film 31. Thus film 31 covers the ends of needle channels 86 of channel member 28, as seen in FIG. 10.

Cover film 31 which covers the outer surfaces of needle channels 86 at the points they intersect the surface 78 of channel member 28 may be made from any of a plurality of readily pierceable film materials. A typical film is a vinyl tape having an adhesive coating, and as disclosed in U.S. Pat. No. 3,779,082, herein incorporated by reference.

In assembling channel member 28 and seal member 26 to each other, projections 81 are aligned with recesses 67 and surfaces 62 and 76 are brought together as shown in FIG. 10. The assembly may be completed by the use of a coating of adhesive wherein the corresponding surfaces of the channel member and the seal member are adhesively bonded to each other about their contiguous mating surfaces. Film 31 is preferably adhesively mounted to the outer surface 78 of channel member 28 as shown in FIG. 10, in the complete assembly of fitting 93.

The second inner surface of fitting 93 includes a first surface portion corresponding to the bottom portion 80, including projections 81, which is in contact with penetration zone 66 of seal member 26, preferably over all of the contiguous surfaces of bottom portion 80 and penetration zone 66. Projections 81, which comprise extensions of needle channels 86, are aligned with, and fit into, recesses 67 in seal member 26, as seen in FIG. 10. Thus are the channel member 28 and seal member 26 rotationally keyed to each other in fitting 93, through the cooperative alignment of needle channels 86, projections 81, and recesses 67. Thus, channels 86 are readily aligned with recesses 67, which are aligned with bottom portions 68, which align with holes 40 of adapter 24; whereby channels 86 are aligned with holes 40 through penetration zone 66 and bottom portions 68.

The central surface portion 84 of the second inner surface is optionally concave, whereby it cooperatively receives the central portion 62 of the first inner surface of seal member 26, which is optionally convex. Thus, central surface portion 84 cooperates in receiving the strengthening and stabilizing central core member 38 of adapter 24. As seen in FIG. 10, surfaces 62 and 84 preferably share a common interface about their contiguous surfaces.

The apparatus of the invention is useful for aseptically transferring material into an enclosure such as tank 10. The tank 10 is preferably adapted for use of the invention by the permanent installation of an adapter 24 in a wall or other outer member of the enclosure as seen generally at 16 in FIG. 1, and in more detail at FIGS. 11, 16, and 18. Preferably the adapter is installed by means of weld 34. When adapter 24 is installed in the tank, it is preferably rotationally aligned with aligning means on a driving apparatus described hereinafter for driving needles through fluid receiver fitting 93 in assembly 12. After the adapter has been installed, a receiver fitting 93 is installed in adapter 24.

Figure 13:
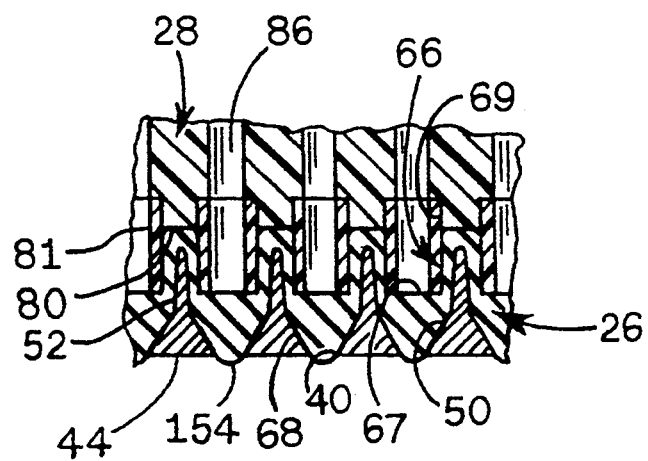
FIG. 13 is a fragmentary cross-section of the fluid receiver assembly of FIG. 12, and is taken at 13—13 of FIG. 12.

Fitting 93 is installed in adapter 24, to make fluid receiver assembly 12, by bringing surface 60 of seal member 26 into surface contact with the surfaces about channel 46, namely, inserting fitting 93 into adapter 24, with seal member 26 facing the adapter. As fitting 93 is inserted into adapter 24, the rotational alignment of vertical channels 54 on adapter 24 with vertical ribs 55 on seal member 26 effects the proper rotational alignment of fitting 93 with adapter 24. Accordingly, bottom portions 68 are aligned such that they fit into channel segments 48 and are thus guided to seat in holes 40 as shown in FIGS. 11, 13, and 16. Thus the adapter, the seal member, and the channel member are jointly configured and adapted to assure the alignment of channels 86 with holes 40, with an intervening pierceable, self-closing portion of the seal member corresponding to penetration zone 66. This alignment assures an unimpeded passage of needles through the fitting 93 along paths prescribed for the needles. With the fitting thus aligned in the adapter, retaining ring 30 is emplaced and secured, whereby the installation of fitting 93 into tank 10 is completed. As retaining ring 30 is tightened, it seats against flange 92 of channel member 28, whereby seal member 26 is compressed between adapter 24 and channel member 28. As seal member 26 is compressed, bottom portions 68 are urged into holes 40. As the compression progresses, additional rubber flows through the holes 40 and extends the original contours of bottom portions 68 further beyond the interior surface 44 of the adapter, such that the combinations of the original bottom portions 68 plus the additional material appear as nipples 154 comprising a greater amount of the rubber material than only the bottom portions 68, on the inside surface of the tank, as seem in, for example, FIG. 11. The view from inside the tank is then as seen in FIG. 12, with the then-invisible weld 34 being represented by a dashed outline.

FIG. 13 shows a fragment of the annular cross-section of the assembly of FIG. 12. It is seen that blocking walls 69 between recesses 67, along with bridging walls 52, prevent inadvertent leakage of transfer material (i.e. material 148 of FIG. 16) between the recesses 67. Also, projections 81 are illustrated as separate elements set into countersunk portions of bottom 80 of channel member 28. Projections 81 can be separate as in FIG. 13 or integral as in FIG. 8.

Fitting 93 is held to adapter 24 by retaining ring 30 seated against flange 92 on channel member 28 and by threads 56 cooperating with threads 57 on retaining ring 30. Thus retaining ring 30 serves as a bridge between the threads 56 on adapter 24 and the flange 92 on channel member 28.

It is seen in FIGS. 10, 11, and 16 that channel member 28 and seal member 26 are in essentially interfacial contact about their contiguous surfaces. FIGS. 11 and 16 show that adapter 24 and seal member 26 are in substantially complete interfacial contact about their contiguous interfacial surfaces. Seal member 26 is held in compressive contact between adapter 24 and channel member 28 by retaining ring 30, which serves as a holding means bridging the channel member and the adapter. It is further seem that the central surface portion 72 of the second surface 60 of seal member 26 engages central core member 38 of adapter 24.

The combination of the adapter 24 and the fluid receiver fitting 93, comprising film 31, channel member 28, and seal member 26 comprises the aseptic receiver assembly 12 which provides access to the interior of the enclosure, such as tank 10, for the insertion of one or more needles, preferably a plurality of needles held together in a needle bundle.

The central axis of the fluid receiver assembly extends through channel member 218, seal member 26, and adapter 24, and thus corresponds with central axis 90 of channel member 28, as shown in FIGS. 8 and 11.

The installation of the adapter 24 into tank 10 leaves an unclosed system, in that holes 40 in the adapter lead directly to the interior of the enclosure. Therefore a fitting 93 is normally kept installed in the adapter at all times in order to have a closed system. After completion of installation of fitting 93 into adapter 24, to form receiver assembly 12, the tank 10 and other associated system components may be sterilized as desired. Typically, steam is used.

Figure 14:
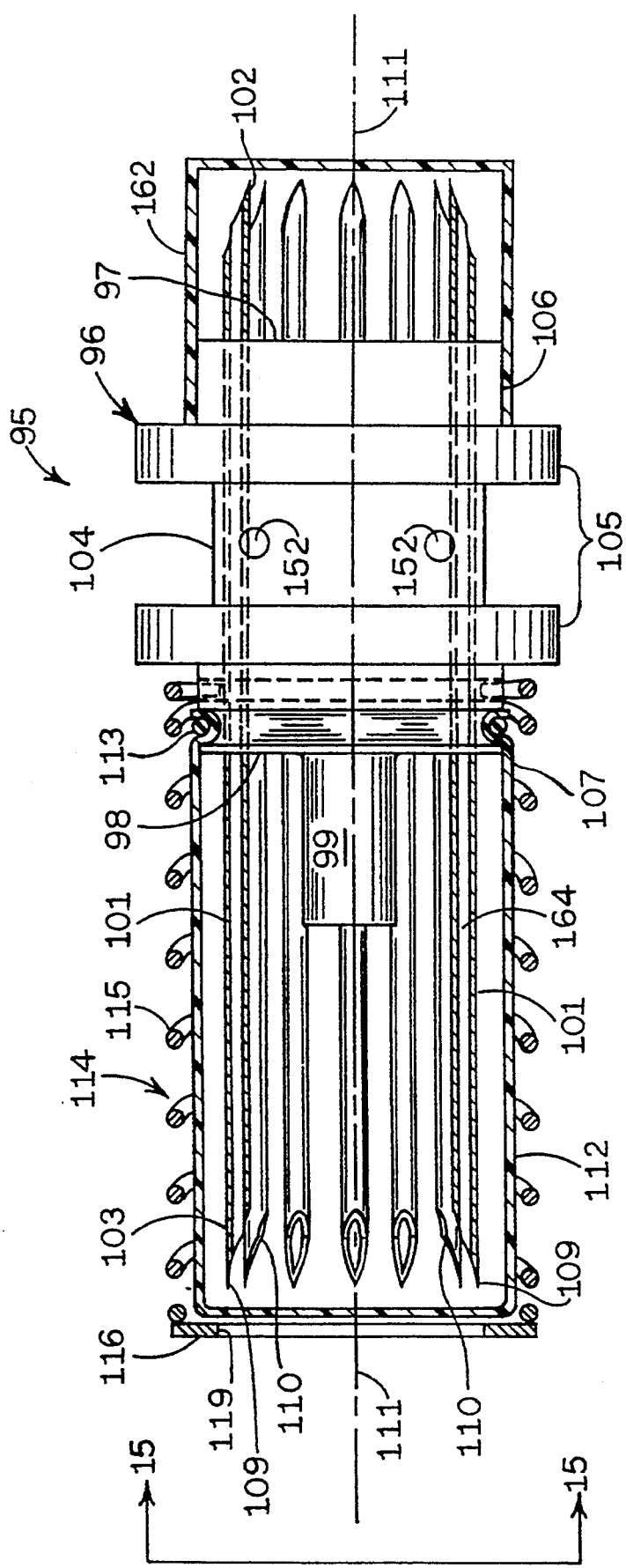
FIG. 14 shows a side view of a needle bundle of the invention, with parts cut away, and including a needle holder, a plurality of needles in the holder, and needle covers.

Referring now to FIGS. 14 and 14A-C, needle bundle 95 comprises a needle holder 36 having a first end 97 and a second end 98. Spacer 99 extends from second end 98. Needle holding channels 100 frictionally hold needles 101. Needle holding channels 100 are seen in FIGS. 14A-14C, with the needles 101 being illustrated in the channels 100 in FIGS. 14 and 16. For purposes of this illustration needles 101 have first ends 102 corresponding to the first end 97 of holder 96. Similarly, second ends 103 of needles 101 correspond to the second end 98 of holder 96. The naming of the first and second ends of the needles and the needle holder can, of course, be reversed. Holder 96 has a groove 104 and a pair of ribs 105 flanking groove 104. First and second adapting lands 106 and 107 respectively can function as surfaces for joining the needle holder to further components used in the practice of the invention.

First end 97 of holder 96 is compatible with receiving a penetrable container closure such as a plastic bung 108 as seen in FIG. 16. FIG. 16 shows two needle ends 102, with the connecting centerline indicating the presence of the rest of the needles behind the cutting surface, view of those needles being blocked by the intervening product material 148.

The spacer 99 on second end 98 is configured and positioned for spacing the second end 98 from a generally planar surface, for example the top surface 78 of channel member 28 in fitting 93, which includes covering film 31, all as seen in FIG. 16. The length of spacer 99, and the distance that it spaces end 98 from a planar surface is preferred to be between about 0.20 and about 0.60 times the distance between the second end 98 of the needle holder and the second ends 103 of the needles 101. As another, and alternate, less preferred measure, spacer 99 is between 0.25 and 0.65 times the distance between first and second ends 97 and 98 of the needle holder 96. Functionally, spacer 99 holds the second end 98 spaced from the assembly 12 a sufficient distance to accommodate flexing outwardly of the needles 101 as they penetrate through the fitting.

Referring back to FIG. 14, the second ends 103 of needles 101 are angled to end tips 109 such that the second ends 103 of needles 101 have angled surfaces 110 disposed in directions transverse to the lengths of the needles, and generally facing toward central axis 111 of needle holder 96.

A flexible, bacteria impermeable, cover 112 entirely encloses the needles 101 on the second end of the needle holder. An acceptable material for cover 112 is a spun-bonded polyolefin such as Tyvek, from DuPont. Cover 112 is held in place by O-ring 113 in a groove on adapting land 107. Cover 112 is penetrable by needles 101.

Abuse resistant cover 114 comprises a difficultly compressible spring 115 and a washer 116. Spring 115 has two wire ends 117 which fit into transverse hole 118 on land 107 and thus securely and rigidly hold cover 114 to the needle holder 96. Ends 117 and hole 118 thus serve as first and second joinder means holding the cover 114 to the needle holder. Washer 116 is bonded to the outer end of spring 115, for example by a weld. The inner perimeter 119 of washer 116 is slightly larger than, and encompasses, an imaginary outer perimeter 120 circumscribed by the tips 109 of needle ends 103.

Figure 19:
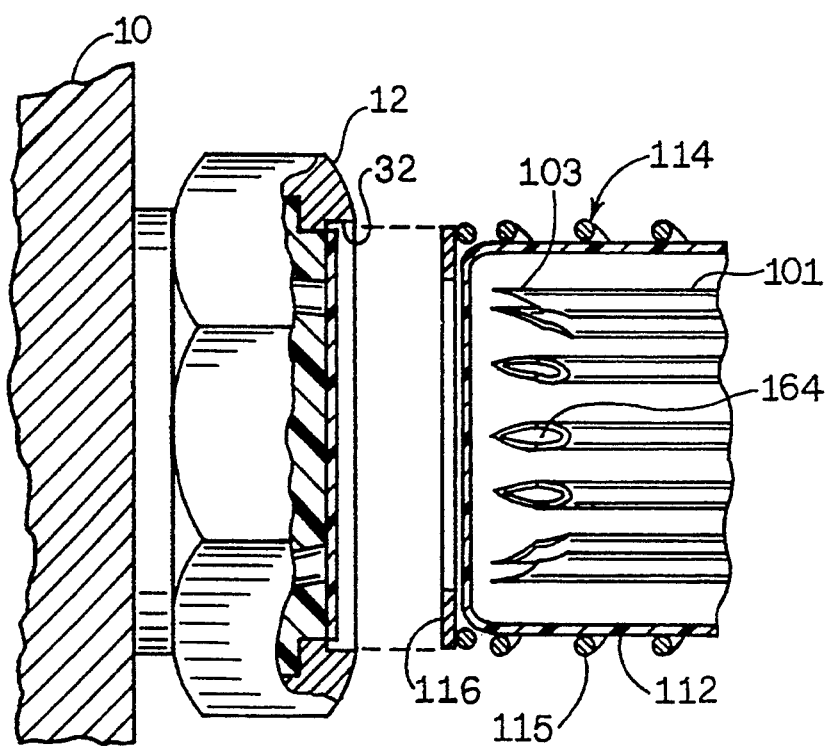
FIG. 19 is a fragmentary view of the receiver assembly and needle bundle as in FIG. 18, with the needle bundle withdrawn from contact with the receiver assembly.
Figure 18:
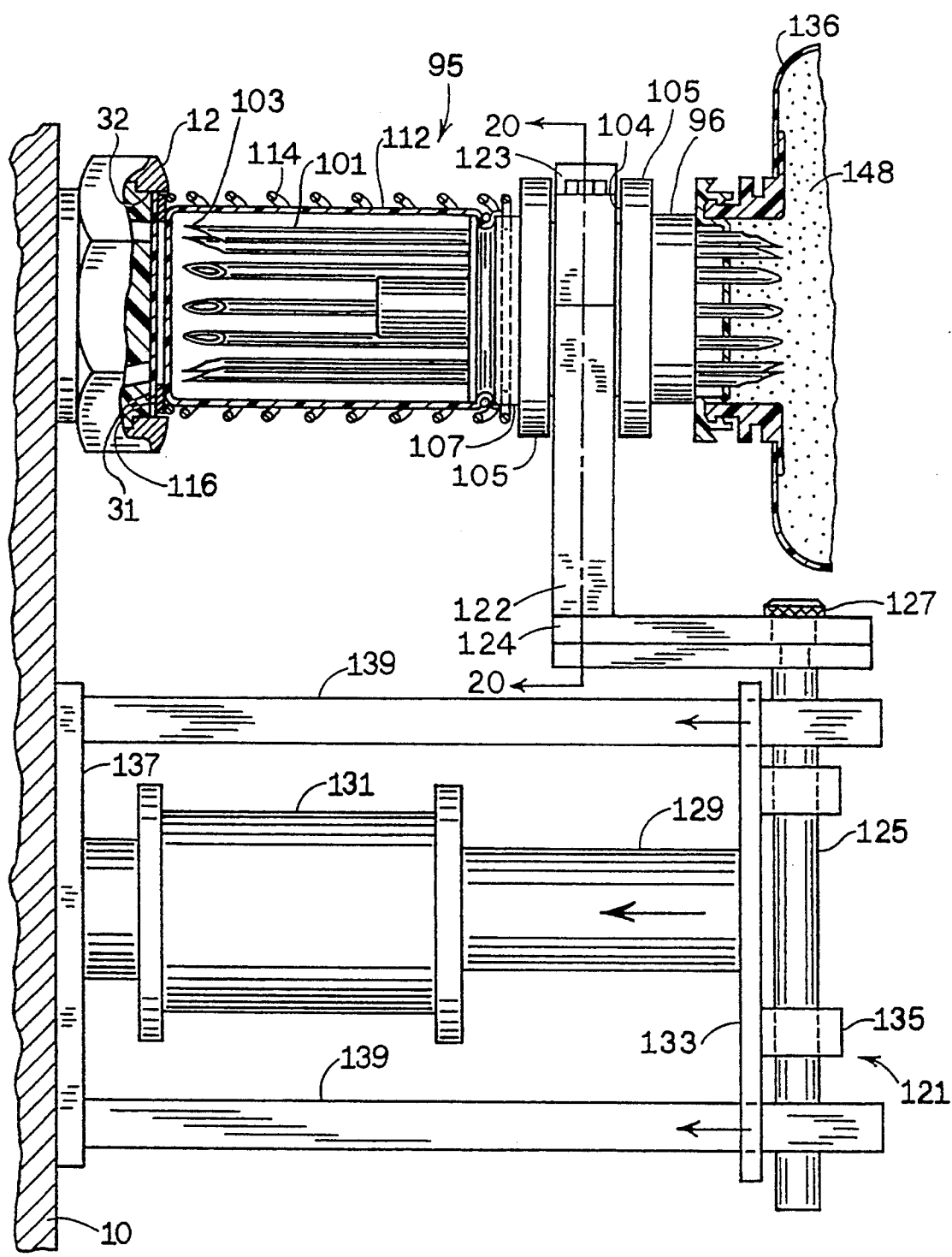
FIG. 18 shows, with parts cut away, the needle bundle, aligned with the receiver assembly, and driving means for pushing the ends of the needles through the receiver assembly.

The outer diameter of washer 116 is only slightly less than the inner diameter of the opening 32 in retaining ring 30. With spring 115 in the uncompressed state, cover 114 extends beyond the ends 103 of needles 101 as seen in FIGS. 14, 18 and 19. Thus, with spring 115 in the uncompressed state, the difficultly compressible spring 115 serves as a functional barrier to physical abuse of the needles from the sides. The needles 10i are generally protected from the end, as by washer 116, except for small objects, which are smaller than the inner perimeter 119 of washer 116. While it is possible for such small objects to avoid washer 116 and contact needles 101, most objects will be deflected by washer 116 either outwardly of the needle bundle, or inwardly of the ring of needles. And since the tips 109 are oriented outwardly of the needle axes, toward imaginary outer perimeter 120 and inner perimeter 119 of the washer, objects deflected inwardly will generally miss tips 109. In general, then, cover 114 protects the needles 101 and needle ends 103 from incidental contact and physical abuse.

Wire ends 117 (FIG. 16) firmly hold cover 114 to the needle holder 96, such that it cannot be removed from holder 96 by an average adult without use of tools. Also, land 107 and spring 115 are so cooperatively designed that the holding of cover 114 is so inflexible, and spring 115 is so difficult to deflect, that the inner perimeter 119 of washer 116 remains dependably aligned around imaginary outer perimeter 120 throughout normal shipping and handling of the needle bundle, as seen from the following.

In addition to the above stated purpose whereby cover 114 protects the needles from outside abuse, the spring 115 selected for use in cover 114 resists substantial manual compression by the average adult user. Namely some mechanical assistance is needed to compress spring 115 enough to expose the tips 109 of needles 101. Thus, the cover 114 is functional to protect the user, and especially the user's hands, from injury by the needles. Further, spring 115 is sufficiently resistant of side loading, with ends 117 installed in hole 118, that it is not manually deflected such that washer 116 might impede the projection of needles 101 past washer 116.

The needle ends 103 are readily uncovered, with mechanical assist, for penetration through the fluid receiver assembly, since the inner perimeter 119 of washer 116 is slightly outside the imaginary outer perimeter 120 circumscribed by the tips 109 of the needle ends 103. Therefore, while washer 116 protects needle ends 103, it does not interfere with the compression of spring 115 of cover 114 and the simultaneous exposure of needle ends 103, thus accommodating the penetration of needle ends 103 through receiver assembly 12 as seen in FIG. 16.

Referring now to FIG. 16, diverging needle channels 86 in receiver assembly 12 are oriented and positioned so that needles 101 pass along paths 145 extending from surface 78 to corresponding holes 40 in adapter 24. Thus, the needles diverge from each other as they are inserted through the fluid receiver assembly 12 to the interior of the enclosure. Paths 145, through film 31, needle channels 86, penetration zone 66 and bottom portions 68 are defined at the time the needles 101 are pushed through the fluid receiver assembly 12 such that the ends 103 of the needles penetrate through bottom portions 68 to the interior of the enclosure. FIG. 16 shows the axes 88 of needle channels 86 and the axes 146 of paths 145 aligned. Minor deviations from that alignment are possible. The axes 88 of channels 86 diverge from each other, traversing inwardly of tank 10, as do the axes 146 of paths 145. Paths 145 usually comprise straight line extensions of needle channels 86, and especially of surfaces 94. It is seen in FIG. 11, and according to the dashed lines 147, that the bottom portions 68 of seal member 26 are aligned with those surfaces 94 of corresponding channels 86 most closely approaching central axis 90 of the channel member 28, and thus of fitting 93.

Figure 17:
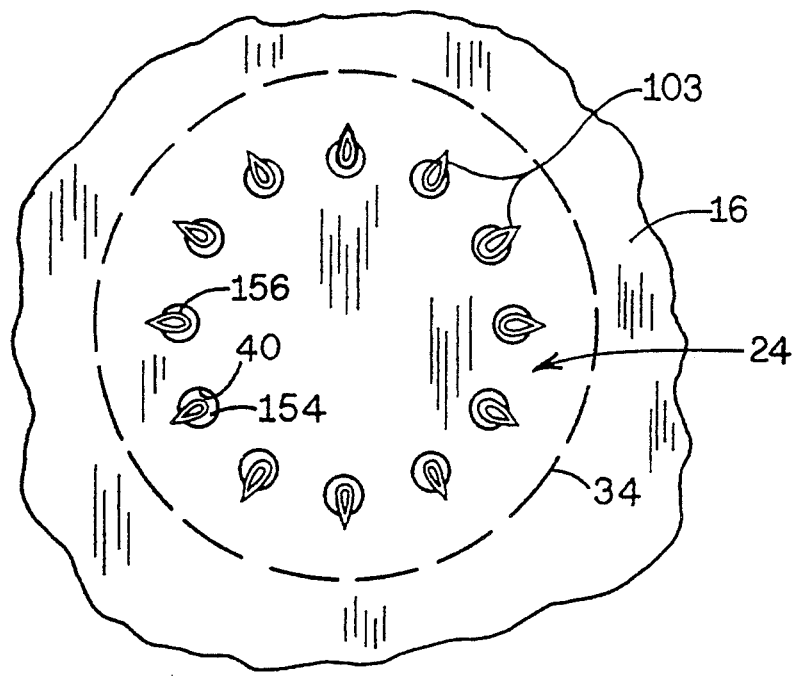
FIG. 17 shows the receiver assembly from the inside of the tank, and is taken at 17—17 of FIG. 16.

With the needles extending through bottom portions 68, the view from inside tank 10 is as shown in FIG. 17. Weld 34 holds adapter 24 in the tank wall 16, and is shown in dashed outline, since the weld is preferably ground flush with, is integral with, and is visually hardly distinguishable from, the inside surface of the tank. Bottom portions 68 extend through holes 40, and into the tank interior as also seen in FIG. 16.

The divergence of needle channels 86 as seen in, for example, FIG. 16, provides a plurality of benefits. It provides for the spreading of the pattern of fluid 148 which is typically transferred from a first enclosure, as at 136 to a second enclosure as at tank 10. The spreading of the pattern of material 148 at the time it is transferred into the second enclosure contributes to a faster mixing of that fluid material 148 into the contents of the second enclosure. Secondly, the resisting force induced in spreading the needle ends provides for a significant base force requirement to be overcome in inserting the needles through the fitting, which base level force, in combination with the difficult compressibility of spring 115, tends to prevent accidental manual insertion of the needles, and to smooth out any tendency toward a jerky insertion. This base level resistance force further assists in the removal of the needles by providing a constant urging of the needles outwardly according to the forces tending to restore the needles to a parallel condition and to restore spring 115 to its rest position.

Referring now to FIG. 18, needle bundle driving means 121 includes pushing collar 122 and cap 123 which are emplaced about the needle holder 96 for pushing of the needle bundle 95, comprising the needle holder 96, the needles 101, and covers 112 and 114, whereby ends 103 of needles 101 penetrate through receiver assembly 12. With the needle bundle fully retracted, namely with the washer 116 withdrawn from opening 32, as seen in FIG. 19, mounting bracket 124 can pivot about arm 125, which facilitates the mounting of the needle bundle to collar 121; and its subsequent dismount. FIG. 18 shows the needle bundle 95 having washer 116 of cover 114 seated, and closely fitted, inside the inner perimeter 32 in retaining ring 30, but before any penetration by ends 103 of needles 101. The combination of needle bundle 95 mounted in driving means 121, and receiver assembly 12, comprises an effective fluid receiver system, for receiving fluid from a first enclosure.

As best seen in FIG. 18, the collar 122 fits into groove 104 between ribs 105. Collar 122 is mounted to bracket 124. Bracket 124 is held to arm 125 by shoulder screw 127. Arm 125 is mounted to shaft 129 of control cylinder 131 through bracket 133 and pivot collars 135. Cylinder 131 is mounted to the tank enclosure 10 by mounting plate 137. Four slide arms 139 extend from mounting plate 137 and are slidably joined to bracket 133.

The primary components used in the practice of the invention are two enclosures, a first one of which contains material to be transferred (source enclosure) and a second one to which the material is to be transferred (receiving enclosure), at least one fluid receiver assembly, and at least one needle bundle.

Figure 20:
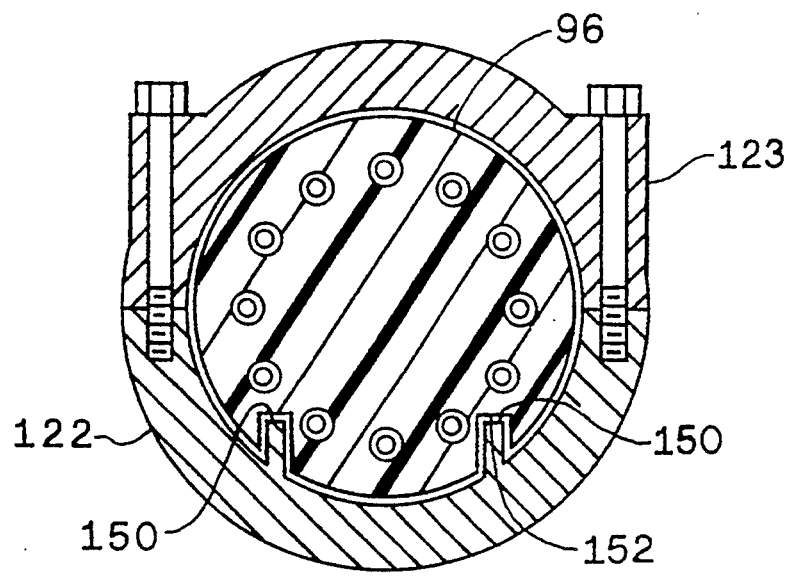
FIG. 20 is a cross-section of the needle bundle and the pushing collar, and is taken at 20—20 of FIG. 18.

Referring to FIG. 18, in order to effect a transfer of material 148 from the first enclosure (container 136) to the second enclosure (tank 10), container 136 is supported adjacent receiver assembly 12, as for example, by an independent stand, or by hangar or other support means attached to tank 10. Collar 122 is fully retracted from assembly 12, as in FIG. 19, and is rotated about pivot arm 125 and away from receiver assembly 12. Groove 104 of needle holder 95 is then placed in pushing collar 122 and aligned so that alignment studs 150 in collar 122 fit into alignment holes 152 in the needle holder 96. Pushing collar 122 is then secured by cap 123 as seen in FIG. 20. The outer surface of film 31 is wiped with a disinfectant such as alcohol to remove any contaminants. The needle bundle 95 is pivoted back to the position shown in FIG. 19, aligning the needles with receiver assembly 12.

Cylinder 131 is then activated. Collar 122 carries needle bundle 95 toward receiver assembly 12 to the alignment checking position shown in FIG. 18. As the needle bundle 95 moves toward receiver assembly 12, the outer perimeter of washer 116 is received inside the rim of inner perimeter 32 of retainer 30, thus assuring the alignment of needles 101 with needle channels 86. Washer 116 seats against cover film 31 as seen in FIG. 18. Flexible cover 112 also stops adjacent film 31. Preferably, the advance of the needle bundle is staged to stop at the position shown in FIG. 18 in order to provide opportunity for the operator to verify the alignment of washer 116 inside the inner perimeter 32 of retaining ring 30.

Power cylinder 131 is then further advanced, pushing ends 103 of needles 101 through cover 112, past washer 116, and through film 31. Both Tyvek cover 112 and vinyl film 31 are easily penetrated by the sharp tips 109 of the needles. As the needles 101 progress inwardly through receiver assembly 12, they enter needle channels 86, and encounter surfaces 94. The divergence of surfaces 94 from the central axis 90 forces the needles to begin their divergence from longitudinal axis 111 of the needle holder 96, which corresponds at that point with longitudinal axis 90 of channel member 28, which further corresponds with the central axis, not separately shown, of receiver assembly 12. With needle end surfaces 110 facing toward central axis 111, they are accordingly facing central axis 90 and diverging surfaces 94, as the needles are inserted into needle channels 86. Thus the angled surfaces 110 are angled similarly to diverging surfaces 94, whereby they are adapted for sliding engagement with surfaces 94. Thus is the sliding of ends 103 of needles 101 along the diverging paths 145 facilitated as the needles are urged through needle channels 86.

The needles thus pass through needle channels 86 and penetrate penetration zone 66 of seal member 26 at recesses 67. The needle ends 103 progress through seal member 26 and emerge from seal member 26 at bottom portions 68 in holes 40, thus completing the definition of paths 145, and reaching their common destination on the interior of the tank.

The surfaces 85 of flow relief recesses 83 are generally spaced from upstanding walls 64 of seal member 26, and penetration zone 66, providing receptive spaces for receiving elastomer material of seal member 26 which flows away from the needles as they are pushed through seal member 26. As needles 101 penetrate seal member 26, they displace the elastomeric/rubber material of seal member 26 along the paths 145. Some of that rubber material flows to flow relief recesses 83, whose walls 85 are spaced from seal member 26. Relief recesses 83 thus relieve some of the pressure caused by that flow of seal member material. Additional of the displaced material of seal member 26 flows ahead of the needle ends, and through holes 40, such that, as ends 103 emerge at bottom portions 68, some of the rubber material, in addition to that which normally forms nipples 154 at bottom portions 68, flows through holes 40 such that nipples 154 are enlarged as the needle ends 103 approach, and begin to penetrate, the surfaces of the nipples and emerge into the interior of the tank enclosure. Accordingly, the enlarged nipples form small collars 156 of rubber material which surround the needles at their place of emergence, as seen in FIGS. 16 and 17.

Preferably the smallest diameter across the holes 40 in adapter 24 is no more than 3 times, most preferably not greater than 2.5 times, the distance across the corresponding needle channels 86. It is also preferably no more than three times the smallest distance across the needles anticipated to be used with the fluid receiver assembly 12. This ensures that the force exerted in pushing the needles through seal member 26 will engender adequate resistance to flow of rubber material through holes 40, so that penetration of the needle tips 109 through the surface of the rubber will assuredly take place before any tearing of the rubber in response to the pushing stress.

As the ends 103 of the needles penetrate the surfaces of the nipples and emerge into the interior of the tank enclosure, spacer 99 approaches, and finally abuts fitting 93 at film 31, thus limiting the distance of travel of the needle bundle 95, and stopping its travel at the appropriate position. Thus, the needle bundle may be installed at the same degree of penetration during each installation without the requirement for visual observation of the distance of penetration. The needle bundle is thus in the position best seen in FIG. 16 and also shown in FIG. 17. In that position, needles 101 provide an open channel for fluid communication between the inside of tank 10 and the inside of container 136.

Pressure differential is applied between container 136 and tank 10 to effect the material transfer. The pressure differential may be applied in a number of ways. One way is by introducing pressure into container 136. Another is by reducing pressure in the tank 10. Yet another is by reducing the volume of container 136. Further, a positive pressure may be applied in container 136 with concurrent drawing of a vacuum in tank 10. Other methods of applying the pressure differential, and thus effecting the transfer will now be obvious to those skilled in the art. Any means of generating an adequate pressure differential between tank 10 and container 136 is effective to cause the flow of material through needles 101.

Figure 24:
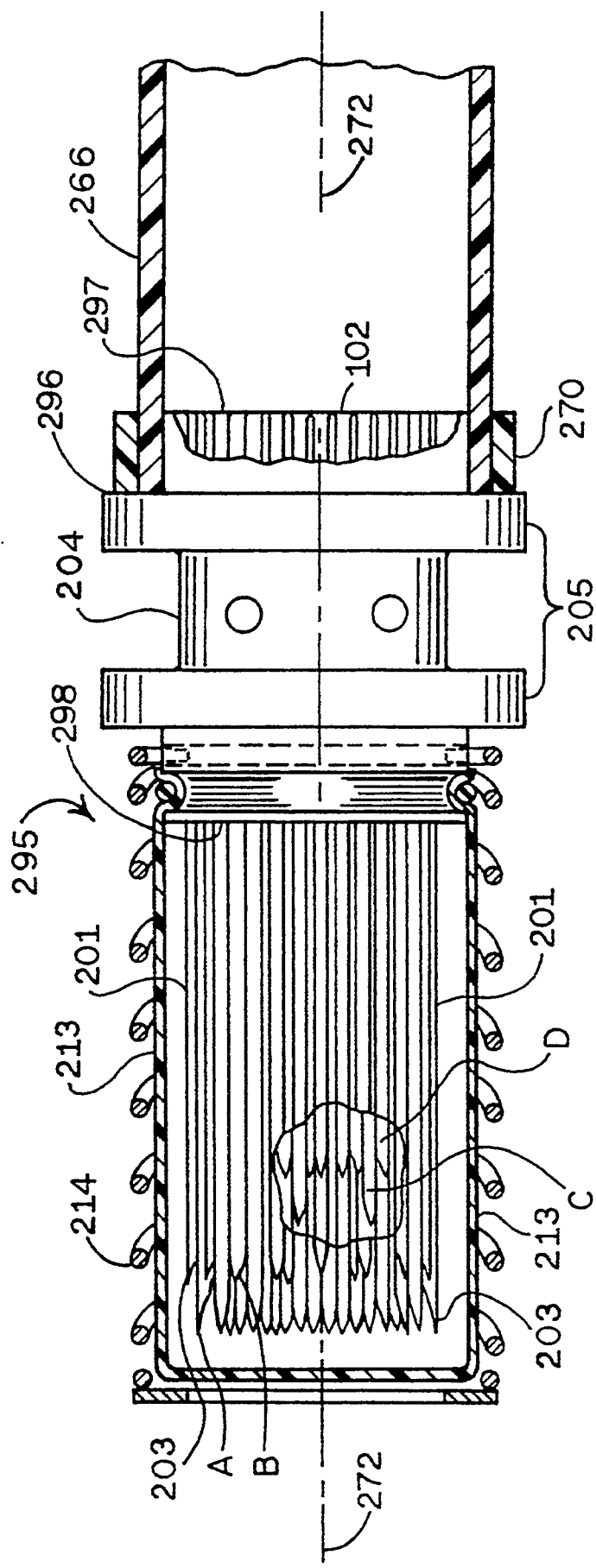
FIG. 24 shows an enlarged side view, with parts cut away, of one end of the fluid transfer assembly of FIG. 22.

The timing of applying the pressure differential can differ for different embodiments, and depends in part on the timing of connecting the two enclosures to the needles. For example, where both enclosures are simultaneously connected to the needles, then timing of establishing the pressure differential can be selected freely. However, if the enclosures are connected sequentially, then it is important that no enclosure having a gauge pressure, either positive, or negative, be connected to the needles until appropriate connection is made on the opposing end of the needles. For example, a tank under vacuum could erroneously draw in contaminated outside air. A tank having a positive gauge pressure could spill its contents out through needles 101. If the needle bundle is connected, as to a tubing, as seen at FIG. 24 hereinafter, appropriate sequential timing accommodation may be made, so long as the contamination sensitivity of the processing system is appropriately respected. Thus a first enclosure having a positive gauge pressure could be connected first, so long as the second enclosure was connected by the time the fluid from the first enclosure reached the second needle bundle.

In the environment shown in FIG. 16, wherein the needles provide open passages between the two enclosures 10 and 136, it is entirely possible that material could be passed in either direction through the needles, depending on (1) the relative pressures in container 136 and tank 10 and (2) the availability of material at the corresponding ends of needles 101 in the source enclosure which has the higher relative pressure, either tank 10 or container 136. In the illustrated embodiment, material 148 is available at needle ends 102, and a positive pressure differential urges material 148 from container 136 into tank 10. Material could likewise be passed from tank 10 to container 136, so long as needle ends 103 are below the top of the material 23 (FIG. 1) in tank 10.

When the desired transfer of material has been completed, any positive gauge pressure in the source enclosure (bag 136) is removed and cylinder 131 is activated in the reverse direction, withdrawing the needles 101 from the fitting 93. As needle ends 103 withdraw into bottom portions 68, the material of collars 156 tends to withdraw to the position held prior to the needle penetration, leaving nipples 154 as viewed from inside tank 10, and as existed prior to penetration of needles 101 through paths 145. As needle ends 103 withdraw from seal member 26, the rubber material which had flowed into flow relief recesses 83 of seal member 26 generally withdraws from recesses 83. This withdrawal of the rubber from collars 156 and flow recesses 83 illustrates the overall closing of the elastomeric material about paths 145 as the needles are withdrawn, thus closing and sealing the fitting 93 against penetration of material 23 from tank 10 outwardly through the fitting 93 along paths 145.

Generally, once the needle bundle 95 is mounted to collar 122 at needle bundle driving means 121, which includes cylinder 131, it generally remains mounted until the transfer has been completed and the needle bundle has been withdrawn from receiver assembly 12. Accordingly, FIG. 16 could show driving means 121, which has been omitted for clarity.

The divergence of the needles as they penetrate receiver assembly 12, and as seen in FIG. 16, puts a bend in needles 101, seen in FIG. 16, along with a corresponding back-pressure generated by the bending and divergence of the needles. With needles 101 driven through assembly 12, the spacing distance between end 98 and the outer surface of receiver assembly 12 is important in order to provide a curvilinear adapting region 140 of the needles 101 between those portions which are rigidly held and positioned in the needle holder 96 and those portions which are urged to diverge from the parallel as in the channels 86. Adapting regions 140 allow the needles a length for conforming to the diverging directions without an abrupt turn, while accommodating the diverging of the needles along their singular diverging paths.

If the fitting 93 is used for transferring substantial quantities of material as in FIG. 16, such as greater than about 100 milliliters, typically all the channels will be used at one time. However, less than all the channels may be used at a given time, For example, the fitting may be used to withdraw samples of material from an enclosure. For that function, one could elect to use only one channel at a time.

After all of the channels in the fitting have been used, the fitting is removed from the adapter, and a new fitting is installed.

It is seen that the functioning of the needle bundle 95 requires that the first ends 102 of the needles 101 extend beyond the first end 97 of the needle holder 96, in order to effect penetration of bung 108 to establish a communicative passage between bag 136 and the interior of tank 10. FIG. 18 shows all of the needle ends 102 behind the cutting plane, whereas FIG. 16 shows only the two needles in the cutting plane. It is further seen that the second ends 103 of needles 101 extend beyond the second end 98 of needle holder 96 and also beyond spacer 99.

It is important that the pattern of needles 101 in the needle bundle 95, and particularly the second ends 103 of the needles be compatible with the pattern of needle channels 86 in the channel member 28 of fitting 93, such that the plurality of needles in the needle bundle can be simultaneously inserted into corresponding needle channels 86 of channel member 28, and pushed through the fluid receiver assembly 12 into the interior of the enclosure. Acceptable needle patterns usually are represented by the fraction a/b, where "a" represents the number of needles, "b" represents the number of needle channels 86 in the fitting, and the fraction can be reduced to 1/X, where "X" is an integer. Examples of needle patterns acceptable for use with the fitting illustrated in FIGS. 2–13, and having 12 channels uniformly spaced in a circular pattern, are shown as patterns of needle holes 100 in needle holder 96, FIGS. 14A, 14B, and 14C.

Also, the channels 86 are generally sized to be only slightly larger, at their narrowest portions, than needles 101, such that the needles fit snugly inside the channels, preferably without substantial friction, but with a close enough fit to ensure that the channels 86 give guiding direction to the needles as they are inserted through the fitting.

The number of channels in channel member 28 is typically the same as the number of needles 101 in the needle bundle 95. In some embodiments, the number of channels in the channel member is a multiple of the number of needles in the needle bundle, whereby a plurality of material transfers can be made using the same channel member, and thus the same fitting 93.

For example, a first needle bundle may be inserted into the receiver assembly in a first enclosure and a first transfer made between the first enclosure and a second enclosure. The first needle bundle is then removed from the receiver assembly in the first enclosure, and a third enclosure is connected, to the first enclosure, through a clean, second needle bundle, by inserting that second needle bundle through the previously unused channels and paths in the same receiver assembly in the first enclosure. Thus a second transfer can be effected between the first and third enclosures, using the same receiver assembly on the first enclosure. It should be understood that the needle bundle used for the second transfer may be the same needle bundle used for the first transfer after the cleaning and sterilization of the needle bundle, whereby the iterated first and second needle bundles are one and the same.

The needle holder 95 can have longitudinal cross-sections other than round, for example rectangular. In that event, its shape may be used as a rotational alignment means as the needle bundle is mounted in collar 122. Collar 122 would, of course, be adapted accordingly, to accommodate the shape of the needle holder. The needle pattern can optionally be adapted to the shape selected for the needle holder.

The fitting 93, comprising the channel member, the seal member, and the cover film, may be separately manufactured, and supplied in a sterile package for installation in the adapter, and for being held in the adapter by retaining ring 30. The needle bundle 95, comprising holder 96, a plurality of needles 101, and covers 112 and 114, may be separately manufactured and supplied in sterile packaging, preferably including cover 162 over ends 102 of the needles.

Container 136, is preferably supplied with material 148 at the material supplier's facility, and is closed with bung 108. The container is then shipped to its user. The needle bundle 95 is attached to bag 136 by pushing needle ends 102 through bung 108. Accordingly, the material 148 in bag 136 can be aseptically transferred into a second enclosure, such as tank 10, by means of the receiver system, including the receiver assembly and the needle bundle, in the manner described above.

The receiver assemblies and the needle bundles illustrated in FIGS. 2–20, and their associated components, are advantageously suited for aseptic transfer of small amounts of fluid. For example, a typical amount of bacteria culture for transfer into a mother culture tank is of the order of about 0.25 liter to 2 liters. For a transfer of such a quantity, the receiver assemblies and needle bundles illustrated above are appropriately sized and adapted with the use of 13 gauge needles, which have a nominal inside diameter of about 0.078 inch, which equals about 0.20 cm.

Such apparatus is also readily adapted for withdrawing a sample of the material 23 from tank 10. For example, the cover film 31 is wiped with a disinfectant and the end of a single hypodermic needle is inserted into tank 10 through one of the needle paths 145. The sample is drawn in the conventional manner of filling a reservoir attached to such a needle. Namely, the plunger is retracted, creating a partial vacuum in the needle reservoir. Material from tank 10 thus flows from the tank, through the needle, and into the needle reservoir. When the appropriate amount of material has been withdrawn from tank 10, the needle is withdrawn from the receiver assembly, thus completing the withdrawal process.

The amount of fluid material which can be transferred between enclosures is controlled by not only the relative pressures in the enclosures, but also by the size of the passages 164 of needles 101, the number of passages, and the effective viscosity of the material being transferred. Effective viscosity includes both the bulk viscosity and the boundary layer effects as the fluid passes through the narrow passages in the several needles. Accordingly, the relative fluid flow rate through a given needle bundle can be estimated by calculating the sum of the areas of passages 164 for all the needles used in a given transfer. For example, the area of the 12 passages 164 illustrated in FIGS. 16–17, using 13 gauge needles can be calculated as follows, using the formula $$Area = \pi r^2$$

$$\text{The area of each needle} = (3.1416) \times \left(\frac{.078}{2}\right)^2 = 0.0048 \text{ sq. in.}$$

The sum of the areas of the 12 needles in the bundle of FIG. 14 = 12 × 0.0048 = 0.0576 sq. in.
The diameter of a tube having an equivalent area is shown by the formula:

$$\text{Diameter} = 2 \times \sqrt{\frac{Area}{3.1416}}$$

Thus a single tube having an interior passage area equivalent to the sum of the passages of the twelve needles of 13 gauge can be calculated as follows:

$$\text{Interior diameter} = 2 \times \sqrt{\frac{.0576}{3.1416}} = 0.27 \text{ inch,}$$

or approximately ¼ inch. Assuming negligible viscosity, and Newtonian fluid flow, one can then project that the maximum theoretical flow rate through a 12 needle bundle of 13 gauge needles will be about the same as the flow rate through a tubing having a ¼ inch inside diameter. The viscosity is, of course, not negligible in many cases. Nor are the boundary layer fluid flow losses negligible, and so the flow rate is usually less than the above calculated maximum. Namely the actual flow rate for this example will most likely be less than the flow in a single tube having an inside diameter of 0.27 inch. The actual flow rate depends largely on the rheological properties of the material being transferred. The viscosity of the material is likely not negligible. Boundary layer flow losses are likely significant. And flow is probably non-Newtonian. Therefore, the actual fluid flow through a 12-needle bundle of 13 gauge needles will likely be significantly less than the flow through a ¼ inch inside diameter tube, for example 20% to 60% less, whereby the amount of material which can effectively be transferred through needle bundle 95 is limited. For example, most processes require critical timing and sequencing of events, whereby it is usually desired to transfer materials into, or out of, the process enclosures over a matter of a few minutes—namely less than 45 minutes, preferably less than 30 minutes, most preferably less than 20 minutes. In some processes, the ideal transfer time is instantaneous, with an acceptable transfer time of no more than about 10 minutes.

Under such processing limitations, the capacity of the needle bundle and the associated receiver assembly takes on added significance. Thus it is desirable to generically define apparatus capable of a range of transfer capacities, which can be employed in making transfers. FIGS. 21–28 illustrate one embodiment of transfer apparatus having a higher fluid flow capacity.

Figure 21:
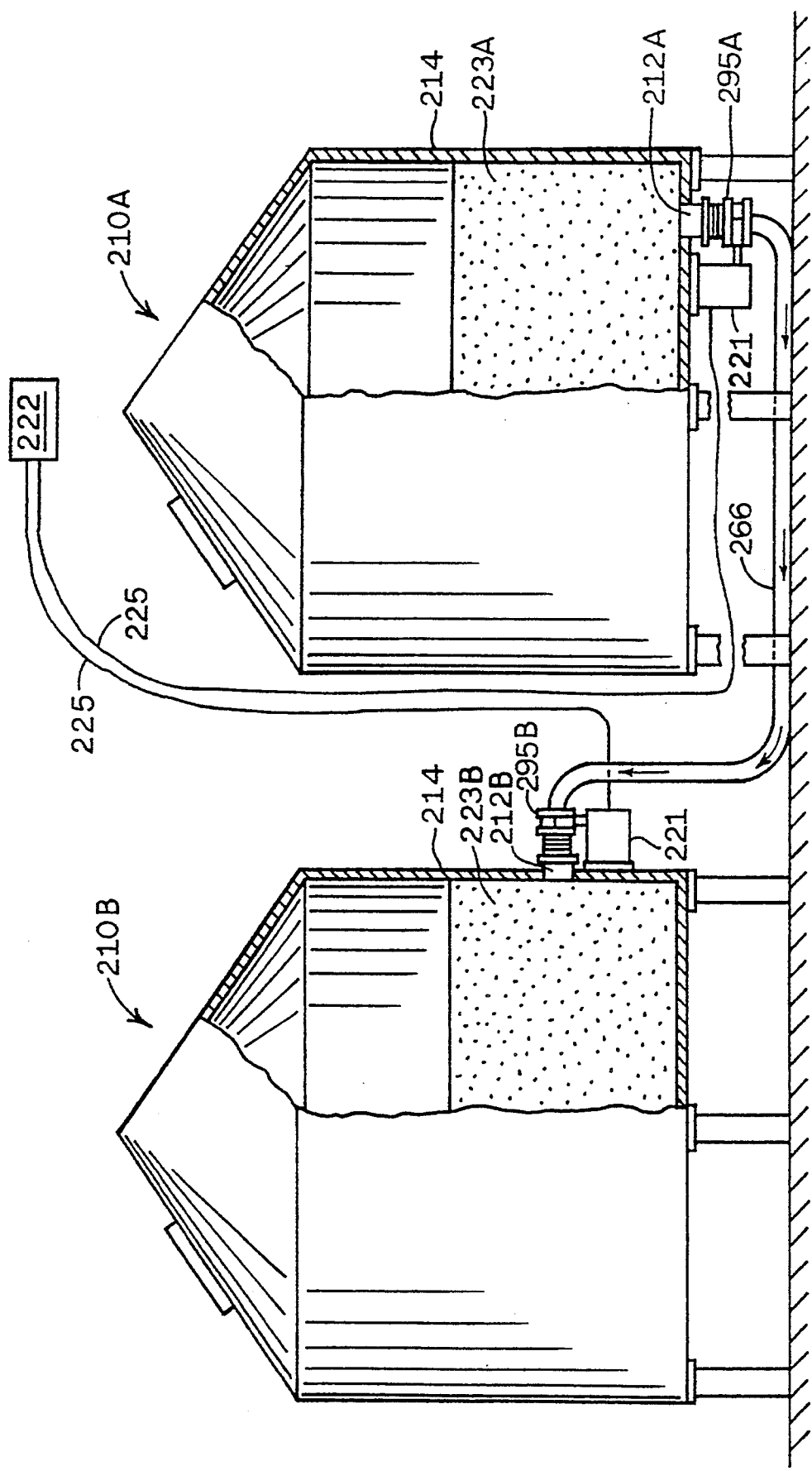
FIG. 21 shows the fluid transfer system for transferring fluid between two tanks.

Referring now to FIG. 21, a first material 223A in tank 210A is being transferred to tank 210B. A first needle bundle 295A is connected to a first receiver assembly 212A installed in tank 210A. A second needle bundle 295B is connected to a second receiver assembly 212B in second tank 210B. Tubing 266 connects the two needle bundles 295A and 295B. With the apparatus configuration shown in FIG. 21, the transfer can be effected by creating an effective pressure differential, whereby the pressure in tank 210A is greater than the pressure in tank 210B, and sufficiently greater to cause material 223A to flow through the two needle bundles and the connecting tubing into tank 210B. Material 223A may be the same as material 223B, or may differ. Usually, the materials differ.

In order to provide an adequate flow rate between two such tanks 210A and 210B, whereby larger quantities of material can be transferred in an acceptable period of time, the component parts and assemblies of the invention are accordingly redesigned, in this illustrated embodiment, as seen in FIGS. 22–28.

For aseptic transfers, a high degree of protection from contaminants is desired. Thus it is preferable that the two needle bundles 295A and 295B, and an appropriate length of the connecting tubing 266 be brought to the transfer site as a single transfer assembly in a sterile package 268. For example, needle bundles 295A and 295B may be attached to tubing 266 under sterile conditions in a laboratory and enclosed in a flexible film package 268 which is conventionally flushed with sterilizing ethylene oxide as part of the process of closing the package.

Figure 23:
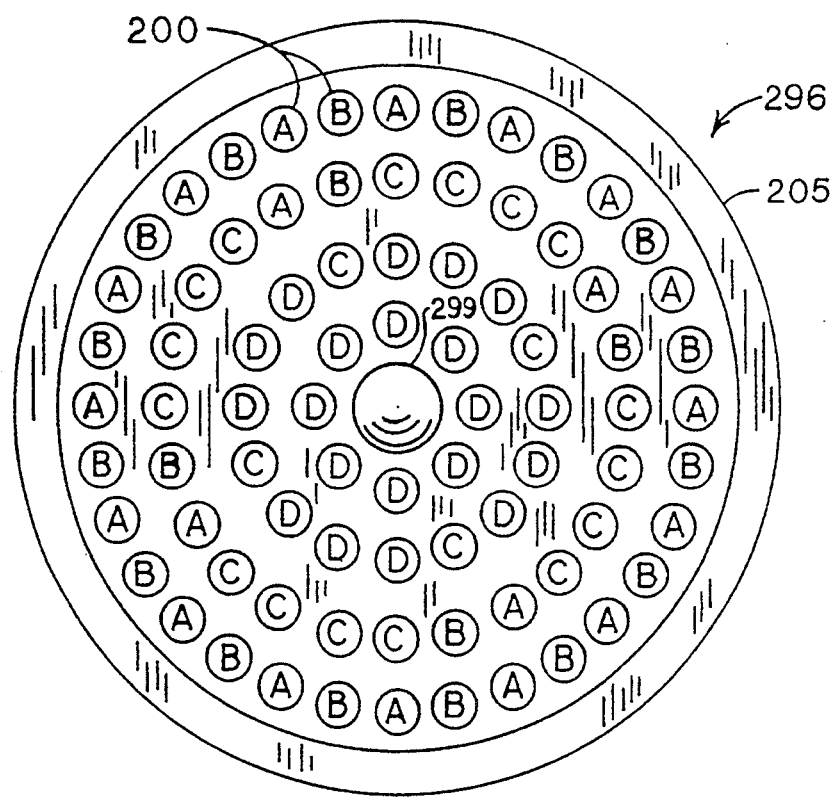
FIG. 23 shows an end view of a needle holder as in FIGS. 14 A–C, and adapted to hold four concentric rows of needles in a high density matrix.

In this example, the desired flow rate of material being transferred is obtained using a tubing 266 having an inside diameter of ¾ inch. The needle bundles 295 have eighty holes, eighty needles, and thus eighty associated passages. Accordingly, the associated receiver assemblies 212A and 212B have eighty available needle paths. In order to accommodate the increased number of passages without unnecessarily increasing the overall sizes of the several elements, the passages are arranged in a matrix. FIG. 23 shows one of the needle holders 296, showing the end 298 which faces the receiver assembly. Spacer 299 corresponds to spacer 99 in FIG. 16. Needle holder 296 has eighty channels 200 arranged in a matrix of four concentric circles. Needle holder 296 has ribs 205 corresponding to ribs 105 in FIG. 14, and a groove 204 corresponding to groove 104 of FIG. 14, as well as alignment holes corresponding to holes 152.

FIG. 24 shows the needle holder 296 assembled into a needle bundle 295, including needles 201, flexible cover 213 and abuse resistant spring cover 214. Covers 213 and 214 correspond to covers 112 and 114 respectively in FIG. 14, with accommodating adjustments in size and resilience. Flexible tubing 266 is secured to needle bundle 295 by clamp 270. Longitudinal axis 272 extends between the needle bundle 295 and tubing 266.

Figure 25:
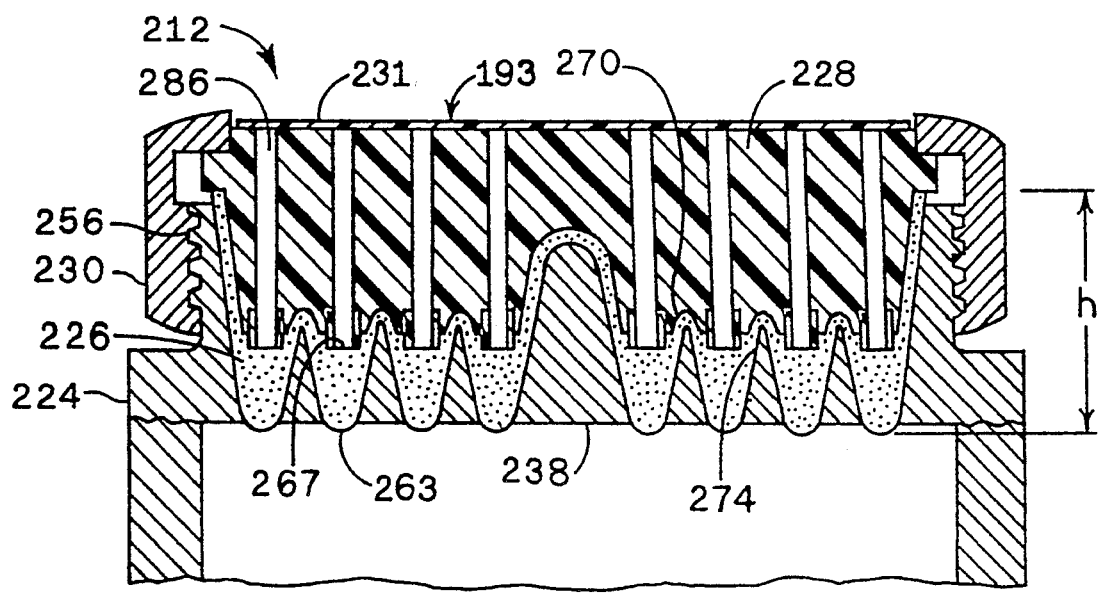
FIG. 25 shows a cross-section of a receiver assembly using adapted embodiments of the seal member, the channel member, and the adapter.

FIG. 25 shows a cross-section of a receiver assembly 212 similar to the assembly 12 shown in FIG. 11, except that it accommodates receiving the needle bundle 295 of FIG. 24, containing the eighty needle matrix.

Figure 26:
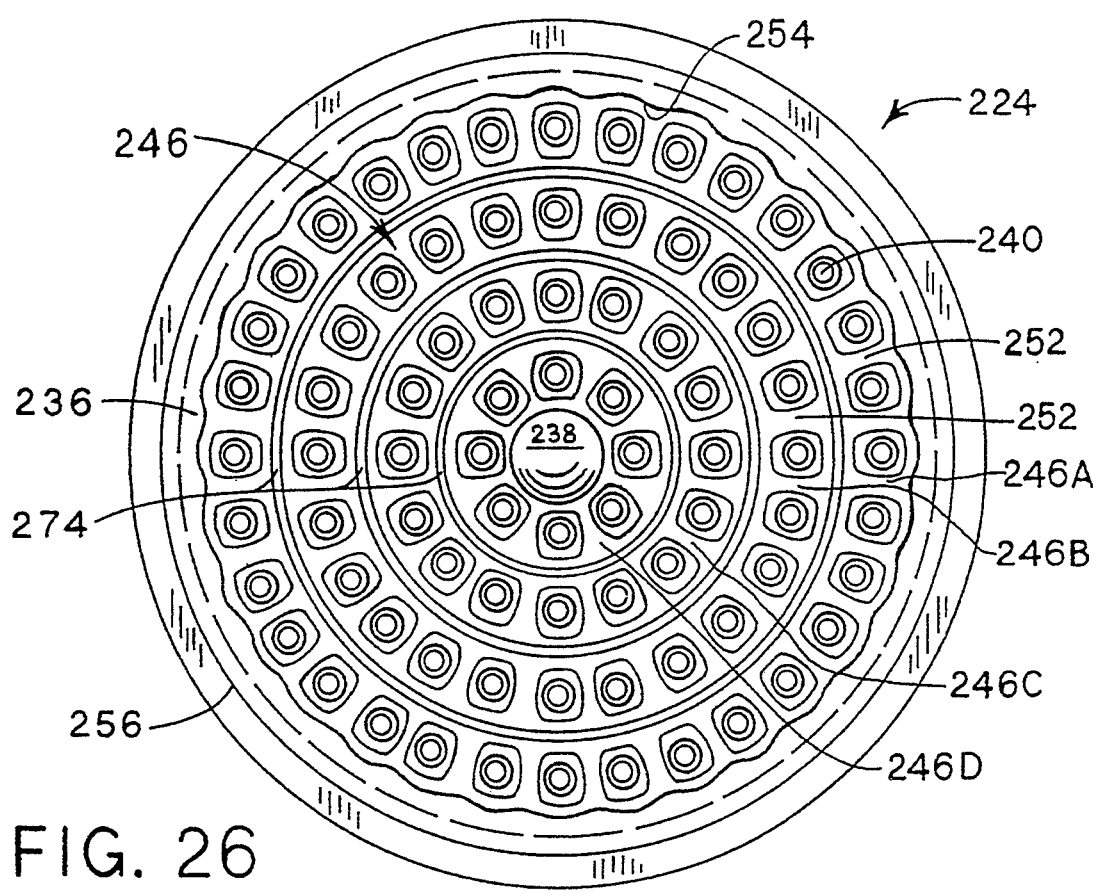
FIG. 26 shows a top view of a second embodiment of an adapter of the invention, having a plurality of concentric rows of holes adapted for use with the needle holder FIG. 23, and in the receiver assembly of FIG. 25.

FIG. 26 shows a top view of the adapter 224 used in receiver assembly 212. In general, the component parts of adapter 224 correspond to the related parts on adapter 24, with appropriate modifications to accommodate the four concentric rows of needle paths. Thus adapter 224 has an outer wall 236, a central core member 238, and a plurality of holes 240 between the outer wall 236 and central core member 238. Continuous channel 246 between outer wall 236 and core member 238 includes bridging rings 274 between secondary channels 246A, 246B, 246C, and 246D, which incorporate the four concentric rings of holes 240. Bridging walls 252 separate the holes radially as in adapter 24 of FIGS. 2–4. Bridging rings 274 separate the concentric rows. Bridging rings 274 and bridging walls 252 also provide the structural strength of the adapter 224 which supports the receiver assembly 212 inwardly of outer wall 236 as the needles 201 are pushed through the receiver assembly. Threads 256 correspond functionally to threads on adapter 24.

Figure 27:
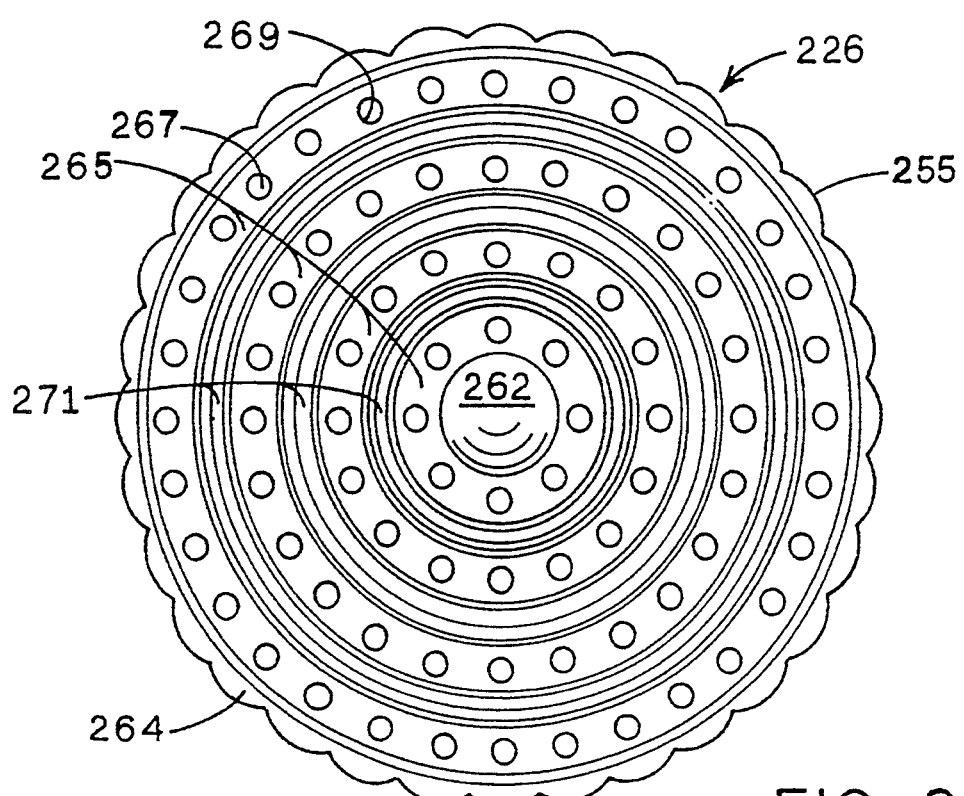
FIGS. 27 and 28 show top and bottom views respectively of a seal member and a channel member adapted for use in the transfer assembly of FIG. 25.

FIG. 27 shows a top view of seal member 226 used in receiver assembly 212, In general, the component parts of seal member 226 correspond to the related parts on seal member 26, with appropriate modifications to accommodate the four rows of needle paths, and to cooperate with the modified adapter 224. Seal member 226 has a generally upwardly projecting central portion 262 and an outer wall 264. Four concentric penetration zones 265 are between outer wall 264 and central portion 262. Penetration zones 265 include recesses 267 aligned with bottom portions 263 (FIG. 25). Blocking walls 269 separate adjacent recesses in each of the concentric penetration zones, Blocking rings 271 separate the four concentric penetration zones.

The bottom surface of seal member 226, of FIG. 25, corresponds generally to the bottom surface 60 described with respect to FIGS. 5 and 6. Thus it has bottom portions 263, an upstanding outer wall portion, and a surface central portion that cooperates with central core member 238 of adapter 224. Surface wall portions (not shown) extend upwardly from, and between, adjacent bottom portions 263, and interface with bridging walls 252 and bridging rings 274 of adapter 224. One bottom portion 263 fits into each of the holes 240 of adapter 224, as illustrated in FIG. 25. Ribs 255 correspond to, and align with, upstanding channels 254 on adapter 224. Channel members 286 are slightly tapered and diverge from a central axis (not shown) of the assembly of FIG. 25, and from each other, all according to the same principles operative in the embodiments of FIGS. 2–20. The divergence, however, is less pronounced as the number of channels is increased.

Figure 28:
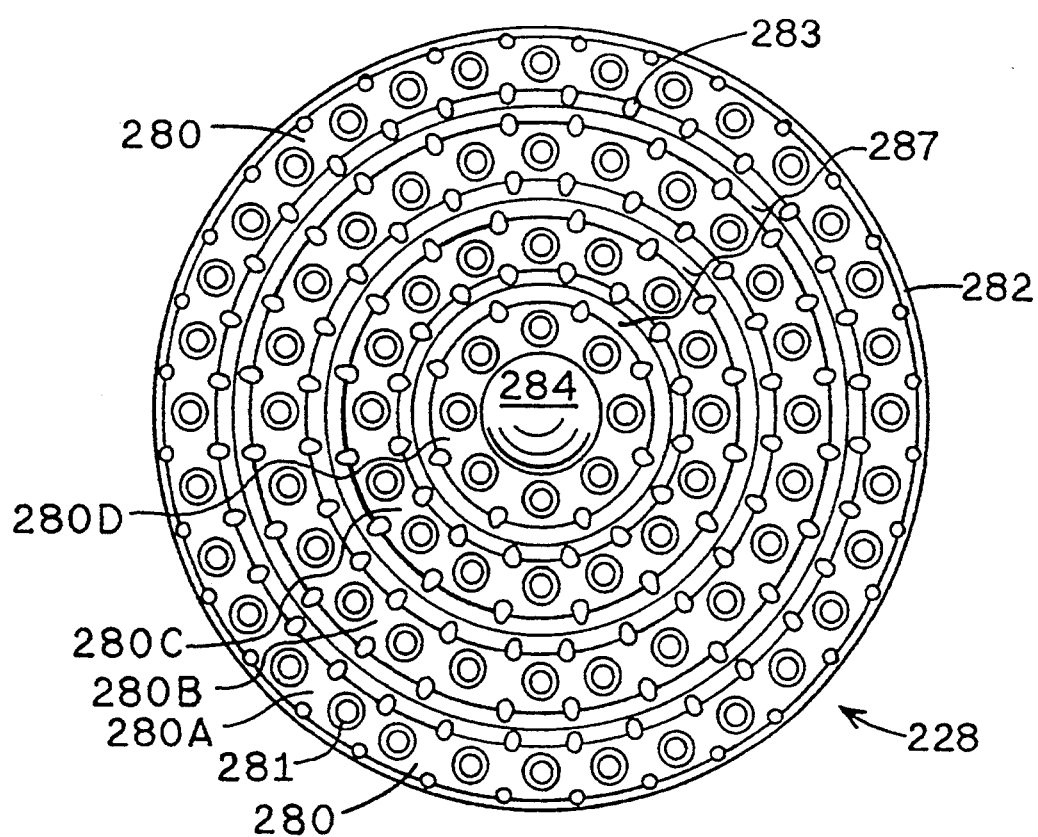

FIG. 28 shows a bottom view of channel member 228, which has bottom portions 280A, 280B, 280C, and 280D, arranged in concentric circles. Bottom portions 280A–D include projections 281. An upstanding outer wall 282 and a third central portion 284 are on opposing sides of bottom portions 280. Needle guide channels 286 extend between the top and bottom walls as seen in FIG. 25. Needle guide channels 286 may diverge from the central axis of the channel member, but where many needles are to be pushed through the receiver assembly 212, the benefits of divergence sometimes may not Justify the total force required to effect divergence of all the needles. And so, in assemblies using a large number of needles, the channels 286 may preferably be aligned with the central axis, or some, but less than all of the channels 286, will diverge, whereby some advantages of divergence are achieved without the requisite force for divergence of all the needles. Seal member 226 and adapter 224 must, however accordingly be adapted.

Recessed concentric grooves 287 separate bottom portions 280A–D and correspond, as mating surfaces, with blocking rings 271 of seal member 226, which generally are supported by bridging rings 274 of adapter 224. Flow relief recesses 283, in recessed grooves 287, preferably flank each needle channel 286, and can extend onto, or across, bottom portions 280, for the same purposes, and according to the same principles as described for relief channels with respect to FIGS. 7–9.

The fluid receiver fitting 193, including channel member 228, seal member 226, and covering film 231 is assembled as described for fitting 93. The fitting is installed in adapter 224 to make receiver assembly 212 as described above for receiver assembly 12, the fitting being held in place by retaining ring 230 as seen in FIG. 25. Once the fitting has been installed a transfer can be made.

Bridging rings 274, bridging walls 252, blocking rings 271, blocking walls 269, and recessed grooves 287 all combine and cooperate in providing a blockage to prevent cross-leakage of the material between the needle paths during the material transfer.

Figure 22:
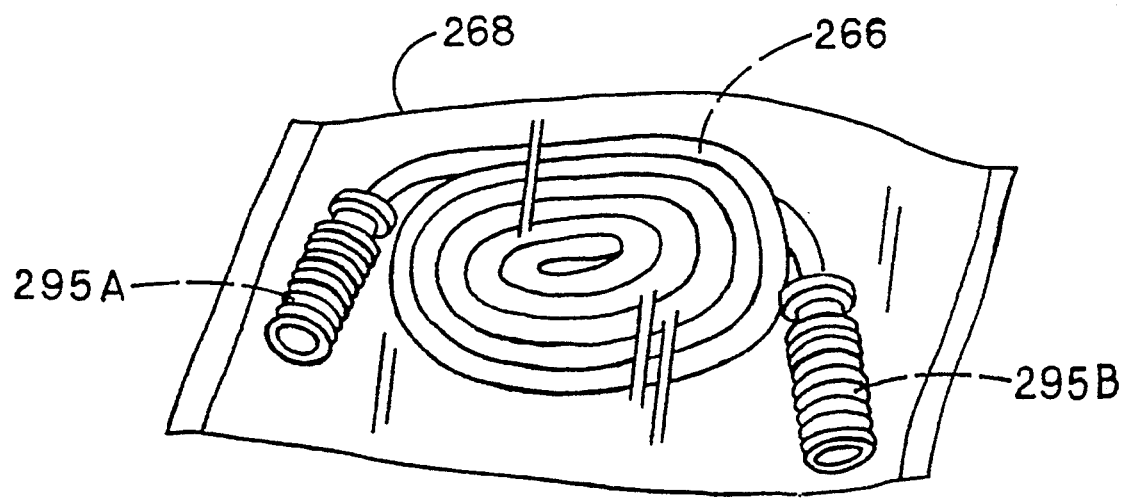
FIG. 22 shows a pictorial view of a sterile flexible fluid transfer assembly in a bag.

In setting up a transfer, the sterile package 268 is opened and the transfer assembly comprising tubing 266 and needle bundles 295A and 295B is removed. Needle bundles 295A and 295B are mounted, with appropriate indexing, in driving means 221 located at both of the respective tanks 210A and 210B. Driving means 221 may be the same as driving means 121 shown in FIG. 18, with appropriate strengthening of the structural members in order to support the driving of eighty needles rather than the twelve needles represented in FIG. 18. Tubing 266 connects the two needle bundles as represented in FIGS. 21, 22, and 24. An appropriate pressure differential is created between the two tanks 210A and 210B. Then both driving means 221 are simultaneously activated by a common control means 222, through control lines 225. The control means 222 can, for example, be a conventional pneumatic controller, with lines 225 being pneumatic lines suitable for carrying pneumatic energy to pneumatic cylinders in drivers 221. Similarly, control means 222 could be a conventional electrical switching means, with wires 225 running to electrical power sources at driving means 221. The actual power and control means, in this particular illustrated embodiment of the method of affecting the transfer, are not critical, so long as both needle bundles 295A and 295B are driven at the same time, or essentially the same time, or in close enough sequencing to avoid contamination of either tank by drawing in of outside air, or spillage of fluid contents.

When the needles are thus driven through both receiver assemblies 212A and 212B, the pressure differential between the two tanks will automatically effect the transfer. When the desired amount of material has been transferred, control means 222 is activated in the opposite direction, and both needle bundles 295A and 295B are preferably simultaneously withdrawn from their respective tanks.

If desired, the pressure differential can be established after the driving of the needle bundles. Also, needle bundle 295A at the source tank can be driven before needle bundle 295B, given a positive gauge pressure in tank 210A, so long as the sequential driving of needle bundle 295B occurs by the time material 223A reaches needle bundle 295B. Indeed such a process could be used as a means of flushing any contaminants from the end of tubing 266 which is adjacent tank 210B. Once the transfer is completed, the needle bundles can be sequentially withdrawn without contaminating either tank, even in the presence of a vacuum in the receiver tank 210B, by withdrawing the needle bundles simultaneously, or by withdrawing needle bundle 295A first, and then withdrawing needle bundle 295B before any air reaches needle bundle 295B.

A tank can, of course have a plurality of receiver assemblies, which provides the tank with the capability of accommodating a plurality of transfers, either simultaneously or sequentially, during a given processing sequence.

Applicant has found that the amount of force required to advance a needle through the seal member, as at 26 in FIG. 6 or at 226 in FIG. 27, increases as the bottom surface 68 or 268 is approached by the tips of the corresponding needles, prior to penetration into the associated tank 10 or 210. Similarly, the stress on the seal member material, and the flowability required of that material, are increased by the approach of the tips of the needles, The stress is particularly acute as the needles approach the inner surfaces of the nipples 154 and have to overcome the surface tension of the inner surface of the seal member at the nipples. Accordingly, the pushing force required to achieve needle breakthrough into the tank is a function of the number of needles which are simultaneously breaking through. And the amount of stress on the seal member material, and its required flowability, are functions of the number of needles which penetrate the seal member at a given time.

Thus, the amount of force required for advancing the needle bundle, and the associated resisting stress, can be reduced by providing that the needles end at different distances from second end 298 of needle holder 296, so that they penetrate the bottom surface at different times during the driving of the needle bundle 295, and thus the needles 201, into the enclosure as at 210A or 210B. FIG. 24 shows the needles 201 ending at four different distances from needle holder end 298. The needles at the greatest distance are labelled "A". The needles at the second greatest distance are labelled "B". The needles at the third greatest distance are labelled "C." The needles at the shortest distance are labelled "D." Needles "C" and "D" are seen through a cut-away that cuts through the outer row of needles, The pattern of needles, and the needle lengths, are illustrated in the end view of the needle holder 295 in FIG. 23. In that illustration, the holes 200 are arranged in the matrix and each hole is labeled A, B, C, or D to indicate the distance of projection, as in FIG. 24, of the needle which will be in that hole.

While needles all the same length can be installed with different distances of projection from end 298, and whereby they can also project different distances from first end 297, it is preferred to use needles differing in length by the amount of the desired differences in their projections, in which case the needles all end in a common plane. While the first ends 102 of the needles in a transfer assembly such as the assembly illustrated in FIG. 22, can project from the first end 297 of the needle holder, preferably the first ends 102 terminate adjacent the first end 297. The needle ends 102 preferably are flared outwardly. The ends can be blunted. Namely the end surface are not sharp. In some embodiments, the needles are preferably flared and blunted, as illustrated at 102 in FIG. 24. Thus, four different lengths of needles are illustrated in FIGS. 23 and 24. As shown therein, exemplary overall lengths of the needles are $3\frac{1}{2}$ inches for the "A" needles, $3\frac{1}{4}$ inches for the "B" needles, 3 inches for the "C" needles and $2\frac{3}{4}$ inches for the "D" needles. The selected lengths can, of course, vary, as can the number of lengths used. As the number of different end distances increases, the potential is increased for reducing the peak force required to effect penetration of all needles. Even two spaced distances will effect some reduction. FIG. 24 shows four distances. Depending on the lengths and stiffness of the needles available, 6 or 8 needle end distances may be advantageous. Usually, no more than 10 different needle end distances are needed to achieve the optimum practical lower peak force. The number of needle lengths may theoretically equal the number of needles. Usually, however, a lesser number is preferred, such as the four lengths shown in FIG. 24.

Needles sized to fit the needle channels 86 and 286 are those which fit closely through the narrowest part of the channels without encountering significant constrictive frictional resistance between the needles and the channels, Typically, the outer diameters of the needles and the smallest inner diameters of the channels will differ by less than 0.010 inch. The channels have a ratio of length to nominal/average diameter of at least 3/1, preferably at least 5/1, and typically about 10/1, whereby the channels guide and align the needles to establish paths which intersect the bottom surface of the seal member in holes 40 or 240 of the respective adapter.

The thickness "t" (FIG. 6) of the seal member 26 or 226 between the end of a channel 86 or 286 and the corresponding bottom portion 68 or 263 is typically significantly greater than the thicknesses of (i) the outer wall 71 or 264 or (ii) the central portion 62 or 262. It is especially important that the thickness "t" provide sufficient bulk of material adjacent the bottom portion to impede pushing of the bulk of that material through the corresponding hole 40 when a needle is pushed through that material. While a small portion of that material is pushed through the hole and forms a collar 156, most of the material is retained between adapter 24 and channel member 26.

Another, and very important, function of the seal member material between bottom portion 68 or 263 and the corresponding channel, is to provide a substantially fluid impenetrable closure of the path 145 when the needle is withdrawn. As the needle is inserted through the seal member material, the preferred rubber material of the seal member is punctured, with a general, but localized, tearing of the rubber as the path 145 is propagated by the advancing needle end 103. Thus the resting configuration of the surfaces of the rubber, in path 145 adjacent a needle 111, represents a somewhat irregular path in the general direction of path 145, when the needle is withdrawn. The resilience of the rubber causes it to tend to close and form the irregular path when the needle is withdrawn. The compression of the seal member, especially between the sloped sidewalls 50 of the channel segments and the bottom 80 of the channel member, further reinforces the tendency of the rubber to close the path as the needle is withdrawn. Thus only very minor amount, if any, of the material (i.e. 23) contained in the tank will enter the irregular path, for example, as the needle is withdrawn. In any event, any such material is trapped by the combination of the irregularity of the path and the compression of the rubber that holds the path closed. And so significant travel of trapped material along the path, either toward channel 86 or back toward the interior of tank 10, is effectively precluded, and the maintenance of the aseptic condition in the tank 10 is assured.

Thus it is seen that the invention provides a novel means for aseptically transferring a fluid from a first enclosure to a second enclosure, including use of novel transfer and receiver apparatus, the environment in at least one of the enclosures being susceptible to contamination from the outside environment. The invention further provides a fitting, and an associated receiver assembly for facilitating making communicative fluid flow connection between the enclosures. The invention also provides a needle holder and a needle bundle useful in effecting the connection and the transfer. A transfer assembly comprising two needle bundles and a connecting flexible tubing accommodates the transfer where both tanks are stationary and not easily transported.

The invention further provides novel methods for transferring material aseptically into an environment which is susceptible to contamination from the outside environment, or for aseptic transfers between enclosures.

Those skilled in the art will now see that certain modifications can be made to the articles, apparatus, assemblies and methods herein disclosed with respect to the illustrated embodiments, without departing from the spirit of the instant invention.

And while the invention has been described above with respect to its preferred embodiments, it will be understood that the invention is capable of numerous rearrangements, modifications and alterations and all such arrangements, modifications and alterations are intended to be within the scope of the appended claims.

Having thus described the invention, what is claimed is:

1. A fluid transfer connector, comprising:
   (a) a needle holder having a plurality of needle holding channels extending between first and second ends;
   (b) a plurality of needles in said needle holder, said plurality of needles having first needle ends extending from said first end of said needle holder, and a corresponding plurality of passages through said plurality of needles; and
   (c) a tube joined to, and extending from, said second end of said needle holder, for carrying fluid, said tube having a first locus in fluid communication with the combination of said plurality of needles such that fluid received from or transferred to said plurality of needles traverses said plurality of needles along said corresponding plurality of passages, leading to a common destination.

2. A fluid transfer connector as in claim 1 and including a resiliently compressible cover having holes therein, receiving said plurality of needles, said cover being joined with said needle holder and extending outwardly beyond said first end of said needle holder and beyond said first ends of said plurality of needles.

3. A fluid transfer connector as in claim 2 wherein said tube has fluid carrying capacity at least as great as the sum of the fluid carrying capacities of said corresponding plurality of passages in said plurality of needles.

4. A fluid transfer connector as in claim 2 and including an index on said needle bundle for cooperatively orienting said needle bundle with respect to a needle bundle driver adapted to drive said needle bundle through a receiver for receiving said needle bundle.

5. A fluid transfer connector as in claim 1 and including a bacteria-impermeable cover covering those portions of said plurality of needles extending from said first end of said needle holder.

6. A fluid transfer connector as in claim 5 wherein said tube has fluid carrying capacity at least as great as the sum of the fluid carrying capacities of said corresponding plurality of passages in said plurality of needles.

7. A fluid transfer connector as in claim 5 and including an index on said needle bundle for cooperatively orienting said needle bundle with respect to a needle bundle driver adapted to drive said needle bundle through a receiver for receiving said needle bundle.

8. A fluid transfer connector as in claim 1 wherein said tube has fluid carrying capacity at least as great as the sum of the fluid carrying capacities of said corresponding plurality of passages in said plurality of needles.

9. A fluid transfer connector as in claim 1 and including an index on said needle bundle for cooperatively orienting said needle bundle with respect to a needle bundle driver adapted to drive said needle bundle through a receiver for receiving said needle bundle.

10. A fluid transfer connector, comprising:
(a) a needle holder having a plurality of needle holding channels extending between first and second ends;
(b) a plurality of needles in said needle holder, said plurality of needles having a corresponding plurality of passages therethrough, said plurality of needles having first ends extending from said first end of said needle holder, said first ends of said plurality of needles being staggered whereby said needle ends extend different distances from said first end of said needle holder; and
(c) a tube joined to, and extending from, said second end of said needle holder, for carrying fluid, said tube having a first locus in fluid communication with the combination of said plurality of needles, such that fluid received from or transferred to said plurality of needles traverses said plurality of needles along said corresponding plurality of passages, leading to a common destination.

11. A fluid transfer connector as in claim 10 wherein said tube has fluid carrying capacity at least as great as the sum of the fluid carrying capacities of said corresponding plurality of passages in said plurality of needles.

12. A fluid transfer connector as in claim 10 and including an index on said needle bundle for cooperatively orienting said needle bundle with respect to a needle bundle driver adapted to drive said needle bundle through a receiver for receiving said needle bundle.

13. A fluid transfer assembly, comprising:
(a) a flexible tube having two ends; and
(b) first and second needle bundles on respective first and second ends of said tube, each said needle bundle comprising (i) a needle holder having a plurality of needle holding channels extending between first and second ends, and (ii) a plurality of needles ill said needle holder, said plurality of needles having first needle ends extending from said first end of said needle holder, and a corresponding plurality of passages through said plurality of needles, said tube having first and second loci in fluid communication with the combination of said plurality of needles in corresponding ones of said first and second needle bundles such that fluid received from or transferred to said plurality of needles in each of said first and second needle bundles traverses the respective said plurality of needles along said corresponding plurality of passages leading to a common destination.

14. A fluid transfer assembly as in claim 13, said first and second needle bundles comprising corresponding first and second bacteria-impermeable covers covering those portions of said plurality of needles extending from said first ends of said needle holders.

15. A fluid transfer assembly as in claim 14 and including an index on said needle bundle for cooperatively orienting said needle bundle with respect to a needle bundle driver adapted to drive said needle bundle through a receiver for receiving said needle bundle.

16. A fluid transfer assembly as in claim 15, further including two enclosures, said tube connecting said two enclosures to each other through said first and second needle bundles.

17. A fluid transfer assembly as in claim 14, further including two enclosures, said tube connecting said two enclosures to each other through said first and second needle bundles.

18. A fluid transfer assembly as in claim 13, said first ends of said plurality of needles being staggered, whereby said needle ends extend first and second different distances from said first ends of said needle holders.

19. A fluid transfer assembly as in claim 18 and including an index on said needle bundle for cooperatively orienting said needle bundle with respect to a needle bundle driver adapted to drive said needle bundle through a receiver for receiving said needle bundle.

20. A fluid transfer assembly as in claim 19, further including two enclosures, said tube connecting said two enclosures to each other through said first and second needle bundles.

21. A fluid transfer assembly as in claim 18, further including two enclosures, said tube connecting said two enclosures to each other through said first and second needle bundles.

22. A fluid transfer assembly as in claim 13 and including an index on said needle bundle for cooperatively orienting said needle bundle with respect to a needle bundle driver adapted to drive said needle bundle through a receiver for receiving said needle bundle.

23. A fluid transfer assembly as in claim 22, further including two enclosures, said tube connecting said two enclosures to each other through said first and second needle bundles.

24. A fluid transfer assembly as in claim 13, further including two enclosures, said tube connecting said two enclosures to each other through said first and second needle bundles.

* * * * *